United States Patent
Kwok et al.

(10) Patent No.: US 7,406,965 B2
(45) Date of Patent: Aug. 5, 2008

(54) FOREHEAD SUPPORT FOR FACIAL MASK

(75) Inventors: Philip R. Kwok, Chatswood (AU); Milind Chandrakant Raje, Wentworthville (AU); Aaron Samuel Davidson, Newport (AU)

(73) Assignee: ResMed Limited, Bella Vista (AU)

( * ) Notice: Subject to any disclaimer, the term of this patent is extended or adjusted under 35 U.S.C. 154(b) by 415 days.

(21) Appl. No.: 10/838,537

(22) Filed: May 5, 2004

(65) Prior Publication Data
US 2005/0022820 A1 Feb. 3, 2005

Related U.S. Application Data

(60) Provisional application No. 60/467,570, filed on May 5, 2003.

(51) Int. Cl.
*A62B 18/02* (2006.01)

(52) U.S. Cl. ............... 128/206.21; 128/205.24; 128/206.27; 128/206.28; 128/207.11; 128/206.12; 128/206.13; 128/205.25; 128/203.29; 128/201.23; 128/201.24; 128/204.26

(58) Field of Classification Search ............ 128/206.24, 128/206.21, 206.27, 206.28, 207.11, 206.12, 128/206.13, 205.25, 203.29, 201.23, 201.24, 128/204.26
See application file for complete search history.

(56) References Cited

U.S. PATENT DOCUMENTS

| 781,516 A | 1/1905 | Guthrie |
|---|---|---|
| 812,706 A | 2/1906 | Warbasse |
| 1,081,745 A | 12/1913 | Johnston et al. |
| 1,192,186 A | 7/1916 | Greene |
| 1,653,572 A | 12/1927 | Jackson |
| 1,926,027 A | 9/1933 | Biggs |
| 2,123,353 A | 7/1938 | Catt |
| 2,245,969 A | 6/1941 | Francisco et al. |

(Continued)

FOREIGN PATENT DOCUMENTS

AU  91/77110  11/1991

(Continued)

OTHER PUBLICATIONS

Mask 1 Photographs, Respironics Inc.. Reusable Full Mask (small) Part #452033 Lot #951108.

(Continued)

*Primary Examiner*—Patricia Bianco
*Assistant Examiner*—Nihir Patel
(74) *Attorney, Agent, or Firm*—Nixon & Vanderhye P.C.

(57) ABSTRACT

A respiratory mask assembly includes a frame and a forehead support secured to the frame. The forehead support includes a joining member secured to an upper portion of the frame and a cushion frame movably mounted to the joining member. One of the joining member and cushion frame includes a pair of shafts and the other of the joining member and cushion frame includes a pair of openings. The pair of shafts are respectively received in the pair of openings to couple the cushion frame to the joining member and enable the cushion frame to move relative to the joining member. Each of the shafts has a non-circular cross section defining a major longitudinal axis that is angled forwardly of a vertical axis of one of the joining member and cushion frame so as to angle toward a front portion of one the joining member and cushion frame.

18 Claims, 41 Drawing Sheets

U.S. PATENT DOCUMENTS

| | | |
|---|---|---|
| 2,248,477 A | 7/1941 | Lombard |
| 2,254,854 A | 9/1941 | O'Connell |
| 2,317,608 A | 4/1943 | Heidbrink |
| 2,371,965 A | 3/1945 | Lehmberg |
| 2,376,871 A | 5/1945 | Fink |
| 2,415,846 A | 2/1947 | Randall |
| 2,438,058 A | 3/1948 | Kincheloe |
| 2,578,621 A | 12/1951 | Yant |
| 2,590,005 A | 3/1952 | Gordon |
| 2,931,356 A | 4/1960 | Schwarz |
| D188,084 S | 5/1960 | Garelick |
| 2,939,458 A | 6/1960 | Lundquist |
| 3,013,556 A | 12/1961 | Galleher |
| 3,182,659 A | 5/1965 | Blount et al. |
| 3,189,027 A | 6/1965 | Bartlett |
| 3,193,624 A | 7/1965 | Webb et al. |
| 3,238,943 A | 3/1966 | Holley |
| 3,315,674 A | 4/1967 | Bloom et al. |
| 3,330,273 A | 7/1967 | Bennett |
| 3,362,420 A | 1/1968 | Blackburn et al. |
| 3,363,833 A | 1/1968 | Laerdal |
| 3,556,122 A | 1/1971 | Laerdal |
| 3,580,051 A | 5/1971 | Blevins |
| 3,700,000 A | 10/1972 | Hesse |
| 3,720,235 A | 3/1973 | Schrock |
| 3,750,333 A | 8/1973 | Vance |
| 3,752,157 A | 8/1973 | Malmin |
| 3,796,216 A | 3/1974 | Schwarz |
| 3,799,164 A | 3/1974 | Rollins |
| D231,803 S | 6/1974 | Huddy |
| 3,830,230 A | 8/1974 | Chester |
| 4,077,404 A | 3/1978 | Elam |
| D250,131 S | 10/1978 | Lewis et al. |
| 4,120,302 A | 10/1978 | Ziegler |
| 4,167,185 A | 9/1979 | Lewis |
| 4,226,234 A | 10/1980 | Gunderson |
| 4,245,632 A | 1/1981 | Houston |
| D262,322 S | 12/1981 | Mizerak |
| 4,304,229 A | 12/1981 | Curtin |
| 4,328,797 A | 5/1982 | Rollins et al. |
| 4,347,205 A | 8/1982 | Stewart |
| 4,354,488 A | 10/1982 | Bartos |
| 4,402,316 A | 9/1983 | Gadberry |
| 4,412,537 A | 11/1983 | Tiger |
| 4,467,799 A | 8/1984 | Steinberg |
| 4,522,639 A | 6/1985 | Ansite et al. |
| 4,558,710 A | 12/1985 | Eichler |
| D285,496 S | 9/1986 | Berman |
| 4,616,647 A | 10/1986 | McCreadie |
| 4,622,964 A | 11/1986 | Flynn |
| 4,655,213 A | 4/1987 | Rapoport et al. |
| 4,665,570 A | 5/1987 | Davis |
| 4,671,271 A | 6/1987 | Bishop et al. |
| 4,677,975 A | 7/1987 | Edgar et al. |
| 4,677,977 A | 7/1987 | Wilcox |
| H397 H | 1/1988 | Stark |
| D293,613 S | 1/1988 | Wingler |
| 4,739,755 A | 4/1988 | White et al. |
| 4,770,169 A | 9/1988 | Schmoegner et al. |
| 4,774,941 A | 10/1988 | Cook |
| 4,782,832 A | 11/1988 | Trimble et al. |
| 4,799,477 A | 1/1989 | Lewis |
| 4,809,692 A | 3/1989 | Nowacki et al. |
| 4,819,629 A | 4/1989 | Jonson |
| 4,821,713 A | 4/1989 | Bauman |
| 4,841,953 A | 6/1989 | Dodrill |
| 4,848,334 A | 7/1989 | Bellm |
| 4,848,366 A | 7/1989 | Aita et al. |
| 4,907,584 A | 3/1990 | McGinnis |
| 4,910,806 A | 3/1990 | Baker et al. |
| 4,919,128 A | 4/1990 | Kopala et al. |
| 4,938,210 A | 7/1990 | Shene |
| 4,938,212 A | 7/1990 | Snook et al. |
| 4,944,310 A | 7/1990 | Sullivan |
| D310,431 S | 9/1990 | Bellm |
| 4,971,051 A | 11/1990 | Toffolon |
| 4,986,269 A | 1/1991 | Hakkinen |
| 4,989,596 A | 2/1991 | Macris et al. |
| 4,989,599 A | 2/1991 | Carter |
| 5,005,568 A | 4/1991 | Loescher et al. |
| 5,005,571 A | 4/1991 | Dietz |
| 5,027,809 A | 7/1991 | Robinson |
| 5,038,776 A | 8/1991 | Harrison et al. |
| 5,042,473 A | 8/1991 | Lewis |
| 5,042,478 A | 8/1991 | Kopala et al. |
| 5,046,200 A | 9/1991 | Feder |
| 5,063,922 A | 11/1991 | Hakkinen |
| 5,069,205 A | 12/1991 | Urso |
| D323,908 S | 2/1992 | Hollister et al. |
| 5,109,839 A | 5/1992 | Blasdell et al. |
| 5,109,840 A | 5/1992 | Daleiden |
| 5,121,745 A | 6/1992 | Israel |
| 5,133,347 A | 7/1992 | Huennebeck |
| 5,140,980 A | 8/1992 | Haughey et al. |
| 5,140,982 A | 8/1992 | Bauman |
| 5,159,938 A | 11/1992 | Laughlin |
| 5,178,138 A | 1/1993 | Walstrom et al. |
| D334,633 S | 4/1993 | Rudolph |
| 5,220,699 A | 6/1993 | Farris |
| 5,231,983 A | 8/1993 | Matson et al. |
| 5,233,978 A | 8/1993 | Callaway |
| 5,243,971 A | 9/1993 | Sullivan et al. |
| 5,245,995 A | 9/1993 | Sullivan et al. |
| 5,265,595 A | 11/1993 | Rudolph |
| 5,279,289 A | 1/1994 | Kirk |
| 5,280,784 A | 1/1994 | Kohler |
| 5,311,862 A | 5/1994 | Blasdell et al. |
| 5,322,057 A | 6/1994 | Raabe et al. |
| 5,322,059 A | 6/1994 | Walther |
| 5,343,878 A | 9/1994 | Scarberry et al. |
| 5,357,951 A | 10/1994 | Ratner |
| 5,372,130 A | 12/1994 | Stern et al. |
| 5,388,571 A | 2/1995 | Roberts et al. |
| 5,404,871 A | 4/1995 | Goodman et al. |
| 5,419,318 A | 5/1995 | Tayebi |
| 5,429,126 A | 7/1995 | Bracken |
| 5,429,683 A | 7/1995 | Le Mitouard |
| 5,431,158 A | 7/1995 | Tirotta |
| 5,438,981 A | 8/1995 | Starr et al. |
| 5,441,046 A | 8/1995 | Starr et al. |
| D362,061 S | 9/1995 | McGinnis et al. |
| 5,477,852 A | 12/1995 | Landis et al. |
| 5,479,920 A | 1/1996 | Piper et al. |
| 5,481,763 A | 1/1996 | Brostrom et al. |
| 5,488,948 A | 2/1996 | Dubruille et al. |
| 5,492,116 A | 2/1996 | Scarberry et al. |
| 5,501,214 A | 3/1996 | Sabo |
| 5,509,404 A | 4/1996 | Lloyd et al. |
| 5,517,986 A | 5/1996 | Starr et al. |
| 5,538,000 A | 7/1996 | Rudolph |
| 5,540,223 A | 7/1996 | Starr et al. |
| 5,542,128 A | 8/1996 | Lomas |
| 5,546,936 A | 8/1996 | Virag et al. |
| 5,558,090 A | 9/1996 | James |
| RE35,339 E | 10/1996 | Rapoport |
| 5,560,354 A | 10/1996 | Berthon-Jones et al. |
| 5,570,682 A | 11/1996 | Johnson |
| 5,570,689 A | 11/1996 | Starr et al. |
| D377,089 S | 12/1996 | Starr et al. |
| 5,592,938 A | 1/1997 | Scarberry et al. |
| 5,608,647 A | 3/1997 | Rubsamen et al. |
| 5,642,730 A | 7/1997 | Baran |
| 5,647,355 A | 7/1997 | Starr et al. |
| 5,647,357 A | 7/1997 | Barnett et al. |

| | | | | | | |
|---|---|---|---|---|---|---|
| 5,649,532 A | 7/1997 | Griffiths | | DE | 4343205 A1 | 6/1995 |
| 5,649,533 A | 7/1997 | Oren | | DE | 29715718 | 10/1997 |
| 5,655,520 A | 8/1997 | Howe et al. | | DE | 197 35 359 | 1/1998 |
| 5,655,527 A | 8/1997 | Scarberry et al. | | DE | 29723101 U1 | 7/1998 |
| 5,657,493 A | 8/1997 | Ferrero et al. | | DE | 298 10846 U1 | 8/1998 |
| 5,657,752 A | 8/1997 | Landis et al. | | DE | 198 17 332 A1 | 1/1999 |
| 5,662,101 A | 9/1997 | Ogden et al. | | DE | 198 08 105 A1 | 9/1999 |
| 5,666,946 A | 9/1997 | Langenback | | DE | 20005346 | 5/2000 |
| 5,685,296 A | 11/1997 | Zdrojkowski et al. | | DE | 29923141 U | 5/2000 |
| 5,687,715 A | 11/1997 | Landis et al. | | DE | 199 54 517 A1 | 6/2001 |
| 5,715,814 A | 2/1998 | Ebers | | DE | 10045183 | 5/2002 |
| 5,724,965 A | 3/1998 | Handke et al. | | EP | 0 054 154 | 10/1981 |
| 5,746,201 A | 5/1998 | Kidd | | EP | 0 252 052 A1 | 1/1988 |
| 5,813,423 A | 9/1998 | Kirchgeorg | | EP | 0 264 772 A1 | 4/1988 |
| 5,832,918 A | 11/1998 | Pantino | | EP | 0 386 605 A1 | 2/1990 |
| D402,755 S | 12/1998 | Kwok | | EP | 0427474 A2 | 5/1991 |
| 5,921,239 A | 7/1999 | McCall et al. | | EP | 0 462 701 A1 | 12/1991 |
| 5,937,851 A | 8/1999 | Serowski et al. | | EP | 0 602 424 | 11/1993 |
| D423,096 S | 4/2000 | Kwok | | EP | 0 608 684 A1 | 8/1994 |
| 6,044,844 A | 4/2000 | Kwok et al. | | EP | 0 0697 225 | 7/1995 |
| D428,987 S | 8/2000 | Kwok | | EP | 178 925 A2 | 4/1996 |
| 6,098,205 A | 8/2000 | Schwartz et al. | | EP | 0 747 078 A2 | 12/1996 |
| 6,112,746 A | 9/2000 | Kwok et al. | | EP | 0 821 978 | 2/1998 |
| 6,119,693 A | 9/2000 | Kwok et al. | | EP | 1099452 | 5/2001 |
| 6,123,071 A | 9/2000 | Berthon-Jones et al. | | EP | 1205205 | 11/2001 |
| 6,152,137 A | 11/2000 | Schwartz et al. | | FR | 2 574 657 A1 | 6/1986 |
| D439,326 S | 3/2001 | Hecker et al. | | FR | 2 658 725 A1 | 8/1991 |
| D443,355 S | 6/2001 | Gunaratnam et al. | | FR | 2 749 176 | 12/1997 |
| 6,257,237 B1 | 7/2001 | Suzuki | | GB | 1395391 | 5/1975 |
| 6,341,606 B1 | 1/2002 | Bordewick et al. | | GB | 1 467 828 | 3/1977 |
| 6,374,826 B1 | 4/2002 | Gunaratnam et al. | | GB | 2145335 A | 3/1985 |
| 6,397,847 B1 | 6/2002 | Scarberry et al. | | GB | 2147506 A | 5/1985 |
| 6,463,931 B1 | 10/2002 | Kwok et al. | | GB | 2 164 569 A | 3/1986 |
| D468,823 S | 1/2003 | Smart | | GB | 2 186 801 | 8/1987 |
| 6,520,182 B1 | 2/2003 | Gunaratnam | | GB | 2 267 648 A | 12/1993 |
| 6,532,961 B1 * | 3/2003 | Kwok et al. ............ 128/206.21 | | JP | 09/216240 A | 8/1997 |
| 6,557,556 B2 | 5/2003 | Kwok et al. | | JP | 11-000397 | 1/1999 |
| 6,595,214 B1 | 7/2003 | Hecker | | WO | WO 80/01044 | 5/1980 |
| D484,237 S | 12/2003 | Lang et al. | | WO | WO 82/03548 | 10/1982 |
| 6,679,261 B2 | 1/2004 | Lithgow | | WO | WO 86/06969 | 12/1986 |
| 6,691,707 B1 | 2/2004 | Gunaratnam et al. | | WO | WO 87/01950 | 4/1987 |
| 6,691,708 B2 | 2/2004 | Kwok et al. | | WO | WO 91/03277 | 3/1991 |
| D492,992 S | 7/2004 | Guney et al. | | WO | WO 92/15353 | 9/1992 |
| 6,860,269 B2 * | 3/2005 | Kwok et al. ............ 128/207.11 | | WO | WO 92/20395 | 11/1992 |
| 7,219,670 B2 * | 5/2007 | Jones et al. ............ 128/206.27 | | WO | WO 93/01854 | 2/1993 |
| 2003/0019496 A1 | 1/2003 | Kopacko et al. | | WO | WO 94/02190 | 2/1994 |
| 2003/0034034 A1 | 2/2003 | Kwok et al. | | WO | WO 94/16759 | 8/1994 |
| 2003/0062048 A1 | 4/2003 | Gradon | | WO | WO 94/20051 | 9/1994 |
| 2003/0089373 A1 | 5/2003 | Gradon | | WO | WO 95/02428 | 1/1995 |
| 2003/0221691 A1 | 12/2003 | Biener et al. | | WO | WO 96/17643 | 6/1996 |
| 2004/0045550 A1 | 3/2004 | Lang et al. | | WO | WO 96/25983 | 8/1996 |
| 2004/0045551 A1 * | 3/2004 | Eaton et al. ............ 128/206.21 | | WO | WO 96/39206 | 12/1996 |
| 2004/0177850 A1 | 9/2004 | Gradon | | WO | WO 97/07847 | 3/1997 |
| 2004/0216747 A1 * | 11/2004 | Jones et al. ............ 128/206.21 | | WO | WO 97/41911 | 11/1997 |
| 2005/0011521 A1 * | 1/2005 | Sprinkle et al. ........ 128/206.21 | | WO | WO 98/04310 | 2/1998 |
| | | | | WO | WO 98/11930 | 3/1998 |
| | FOREIGN PATENT DOCUMENTS | | | WO | WO 9812965 | 4/1998 |
| | | | | WO | WO 98/18514 | 5/1998 |
| AU | 94/64816 B | 12/1994 | | WO | WO 98/26829 | 6/1998 |
| AU | 95/16178 B | 7/1995 | | WO | WO 98/26830 | 6/1998 |
| AU | 32914/95 | 2/1996 | | WO | WO 98/34665 | 8/1998 |
| AU | 9459430 | 2/1996 | | WO | WO 9834665 | 8/1998 |
| AU | A 41018/97 | 4/1998 | | WO | WO 98/24499 | 9/1998 |
| AU | 89312/98 | 1/1999 | | WO | WO 98/48878 | 11/1998 |
| CA | 1039144 | 9/1928 | | WO | WO 9943375 | 9/1999 |
| DE | 459104 | 4/1928 | | WO | WO 99/58181 | 11/1999 |
| DE | 701 690 | 1/1941 | | WO | WO 00/78384 | 2/2000 |
| DE | 159396 | 6/1981 | | WO | WO 00/57942 | 10/2000 |
| DE | 3015279 A1 | 10/1981 | | WO | WO 00/78384 | 12/2000 |
| DE | 3345067 A1 | 6/1984 | | WO | WO 0078381 | 12/2000 |
| DE | 3537507 | 4/1987 | | WO | WO 01/97892 | 12/2001 |
| DE | 3539073 | 5/1987 | | WO | WO 2003/059427 | 7/2003 |
| DE | 4004157 C1 | 4/1991 | | WO | WO/2004078228 | 2/2004 |

| | | |
|---|---|---|
| WO | WO 2004022144 | 3/2004 |
| WO | WO 2004022145 | 3/2004 |

OTHER PUBLICATIONS

Mask 2 Photographs, Puritan—Bennett, Adam Curcuit, Shell Part #231700, Swivel Part #616329-00, Pillows (medium) Part #616324.
Mask 3 Photographs, DeVilbiss Healthcare Inc., Devilbiss Seal-Ring and CPAP Mask Kit (medium), Part #73510-669.
Mask 4 Photographs, Respironics Inc., Monarch Mini Mask with Pressure Port Part #572004, Monarch Headgear, Part #572011.
Mask 5 Photographs, Healthdyne Technologies, Nasal CPAP Mask (medium narrow), Part #702510.
Mask 6 Photographs, Healthdyne Technologies, Soft Series Nasal CPAP Mask, Part #702020.
Mask 7 Photographs, DeVilbiss Healthcare Inc., Small Mask and Seal Rings, Part #73510-668.
Mask 8 Photographs, Respironics Inc., Reusable Contour Mask (medium), Part #302180.
Mask 9 Photographs, Healthdyne Technologies, Healthdyne Large Headgear.
Mask 10 Photographs, Respironics Inc., Soft Cap (medium), Part #302142.
Mask 11 Photographs, Weinmann: Hamburg, Nasalmaskensystem mit Schalldämpfer (medium), Part #WN23105.
Mask 12 Photographs, Life Care.
Mask 13 Photographs, Healthdyne Technologies.
Mask 14 Photographs, King System.
Mask 15 Photographs, Respironics Inc., Pediatric Mask.
Mask 16 Photographs, Hans Rudolph Inc.. Hans Rudolph Silicone Rubber Face Mask/8900.
Photograph of Weinmann Mask, acquired prior to 1998.
Somotron CPAP-Gerat WM 2300 Instruction Manual, Weinmann Hamburg, 11 pages, 1991.
9 photographs of Weinmann mask, WM 23122, 1991.
The ResMed Range of Mask Systems, product brochure, Nov. 1995, 4 pages.
Product Brochure for ResMed "Sullivan® Mirage™—The Mirage is Real. A Perfect Fit—First Time," ©1997 ResMed Limited, 4, pages.
Product Brochure for ResMed "Sullivan® Mirage™—The Mirage is Real. A Perfect Fit—First Time," ©1998 ResMed Limited, 4 pages.
Chinese Office Action, Appln. 200410038106.7 dated Jun. 15, 2007 w/English translation.

* cited by examiner

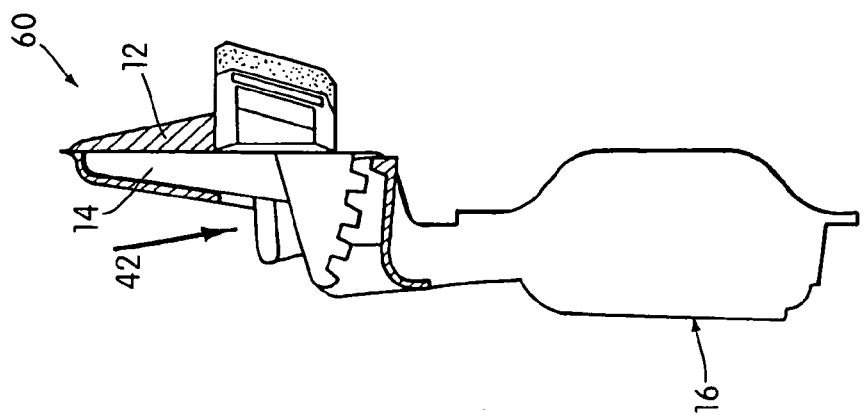
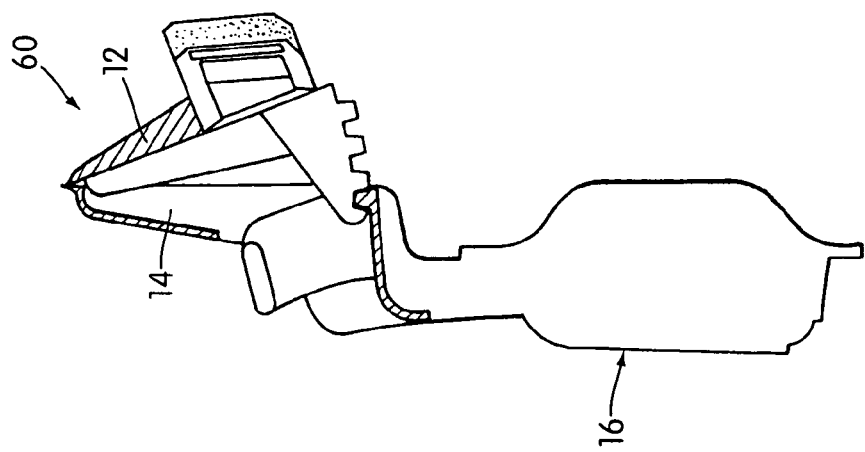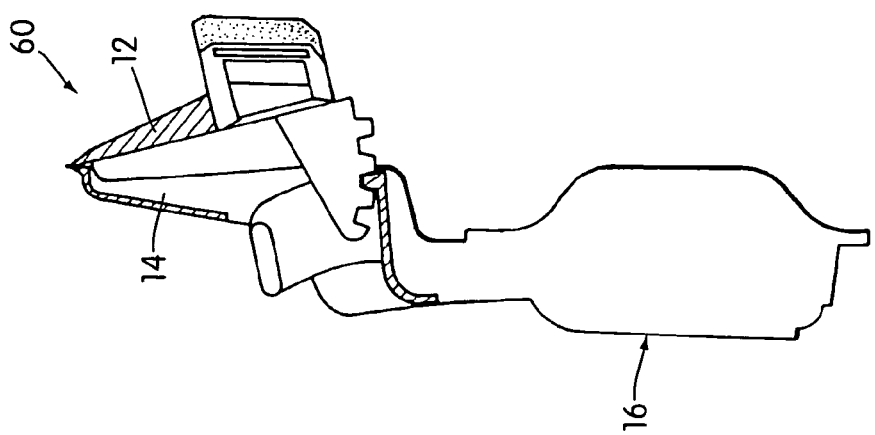

FOREHEAD SUPPORT FOR FACIAL MASK

CROSS REFERENCE TO PRIORITY APPLICATION

This application claims the benefit of U.S. Provisional Application No. 60/467,570, filed May 5, 2003, incorporated herein by reference in its entirety.

FIELD OF THE INVENTION

The present invention relates to a forehead support for a facial mask used to supply breathable gas to a wearer's airways.

The invention has been developed primarily for use in supporting a nasal mask used in Continuous Positive Airway Pressure (CPAP) treatment of, for example, Obstructive Sleep Apnea (OSA) and other ventilatory assistance treatments such as Non-Invasive Positive Pressure Ventilation (NIPPV) and will be described hereinafter with reference to this application. However, it will be appreciated that the invention is not limited to these particular uses and is also suitable for use with, for example, full-face (i.e., nose and mouth) masks.

BACKGROUND OF THE INVENTION

CPAP treatment is a common ameliorative treatment for breathing disorders including OSA. CPAP treatment, as described in U.S. Pat. No. 4,944,310, provides pressurized air or other breathable gas to the entrance of a patient's airways at a pressure elevated above atmospheric pressure, typically in the range 4-20 cm $H_2O$.

It is also known for the level of treatment pressure to vary during a period of treatment in accordance with patient need, that form of CPAP being known as automatically adjusting nasal CPAP treatment, as described in U.S. Pat. No. 5,245,995.

NIPPV is another form of treatment for breathing disorders which can involve a relatively higher pressure of gas being provided in the patient mask during the inspiratory phase of respiration and a relatively lower pressure or atmospheric pressure being provided in the patient mask during the expiratory phase of respiration.

In other NIPPV modes the pressure can be made to vary in a complex manner throughout the respiratory cycle. For example, the pressure at the mask during inspiration or expiration can be varied through the period of treatment, as disclosed in the applicant's international PCT patent application No. PCT/AU97/00631.

Typically, the ventilatory assistance for CPAP or NIPPV treatment is delivered to the patient by way of a nasal mask. Alternatively, a mouth mask or full face mask or nasal prongs can be used. In this specification any reference to a mask is to be understood as incorporating a reference to a nasal mask, mouth mask, full face mask or nasal prongs, unless otherwise specifically indicated.

In this specification any reference to CPAP treatment is to be understood as embracing all of the above described forms of ventilatory treatment or assistance.

A CPAP apparatus broadly comprises a flow generator constituted by a continuous source of air or other breathable gas such as a hospital piped supply or a blower. In the latter case, an electric motor drives the blower and is typically controlled by a servo-controller under the control of a micro-controller unit. In either case, the gas supply is connected to a conduit or tube which in turn is connected to a patient nasal or full-face mask which incorporates, or has in close proximity, an exhaust to atmosphere for venting exhaled gases. Examples of prior art nasal masks are shown in U.S. Patent Nos. 4,782,832 and 5,243,971.

The supply conduit delivers gas into a chamber formed by walls of the mask. The mask includes a cushion positioned against the wearer's face and is normally secured to the wearer's head by straps. The straps are adjusted to pull the mask against the face to achieve a gas tight seal between the cushion and the wearer's face.

A problem that arises with existing masks is that with the use of straps, the mask is compressed against the wearer's face and may push unduly hard on the wearer's nose. Additionally, the mask may move around the wearer's face. Thus, there has been hitherto provided a forehead support, which provides a support mechanism between the mask and the forehead. This forehead support prevents both the mask from pushing too strongly against the wearer's nose and/or facial region as well as minimizing movement of the mask with the addition of a contact point between the mask and the wearer's head thereby reducing uncomfortable pressure points. Additionally, the forehead support can be arranged to prevent the gas supply conduit from contacting the wearer's forehead or face.

Forehead supports with a single cushion and a single contact point on the forehead are known.

The applicant's U.S. patent application Ser. No. 09/008,708 relates to a substantially rigid one-piece forehead support having a pair of forehead cushions mounted at each outer end of the support. This forehead support is connected to the top of a facial mask and includes an adjustment mechanism to allow the spacing between the top of the facial mask and the forehead support to be altered between predetermined positions to alter the angle of the mask relative to the wearer's head to suit the wearer's facial topography.

The applicant's Australian provisional patent application No. PP9499 relates to a forehead support having a pair of pivotable arms that each have a forehead cushion mounted at their distal end. This forehead support is connected to the top of a mask and includes an adjustable mechanism to allow the angle between the arms to be altered between predetermined positions to alter the angle of the mask relative to the wearer's head to suit the wearer's facial topography.

It is an object of the present invention to provide an alternate form of forehead support.

SUMMARY OF THE INVENTION

Accordingly, in a first aspect, the present invention provides a forehead support adapted to be secured to a respiratory mask, said forehead support including a joining member for securing to the mask and a cushion frame pivotally mounted to the joining member, wherein: the cushion frame is adapted to locate one or more forehead cushions; the cushion frame is adapted to pivot relative to the joining member; and the cushion frame is selectively lockable at two or more predetermined angular positions relative to the joining member.

In a second aspect, the present invention provides a respiratory mask assembly comprising a respiratory mask and a forehead support adapted to be secured to the mask, said forehead support including a joining member for securing to the mask and a cushion frame pivotally mounted to the joining member, wherein: the cushion frame is adapted to locate one or more forehead cushions; the cushion frame is adapted to pivot relative to the joining member; and the cushion frame is selectively lockable at two or more predetermined angular positions relative to the joining member.

The cushion frame is preferably T-shaped and includes a forehead cushion at each end of the upper portion of the T.

Preferably, one of the cushion frame or joining member includes a tongue adapted to be received in one of at least two grooves provided on the other of the cushion frame or joining member so as to lock the cushion frame and joining member at one of the two or more predetermined angular positions.

More preferably, a pair of the tongues are provided on the cushion frame and at least two pairs of grooves are provided on the joining member.

The tongue(s) is/are preferably provided on a semi-rigid member which is adapted to permit the tongue(s) to be moved out of engagement with the grooves by manual manipulation of the member. The tongue(s) is/are preferably connected to a button adapted to protrude from the cushion frame to facilitate manual manipulation of the member.

The cushion frame preferably includes means to connect a head strap thereto.

The mask preferably also include means to connect a head strap thereto.

The joining member can be produced from, for example, polypropylene or polycarbonate.

The mask can include a mask shell and a mask cushion. The mask shell can be produced from, for example, polypropylene or polycarbonate.

The cushion frame can be produced from, for example, polypropylene or polycarbonate.

BRIEF DESCRIPTION OF THE DRAWINGS

Preferred embodiments of the invention will now be described, by way of examples only, with reference to the accompanying drawings in which:

FIG. 12 is a cross sectional view of the forehead support shown in FIG. 9 with the tongue and grooves engaged at the third of four positions;

FIG. 13 is a cross sectional view of the forehead support shown in FIG. 9 with the tongue and grooves engaged at the fourth of four positions;

FIG. 14 is a cross sectional view of the forehead support shown in FIG. 9 with the tongue free of engagement with the grooves;

DETAILED DESCRIPTION OF PREFERRED EMBODIMENTS

Figure 1:
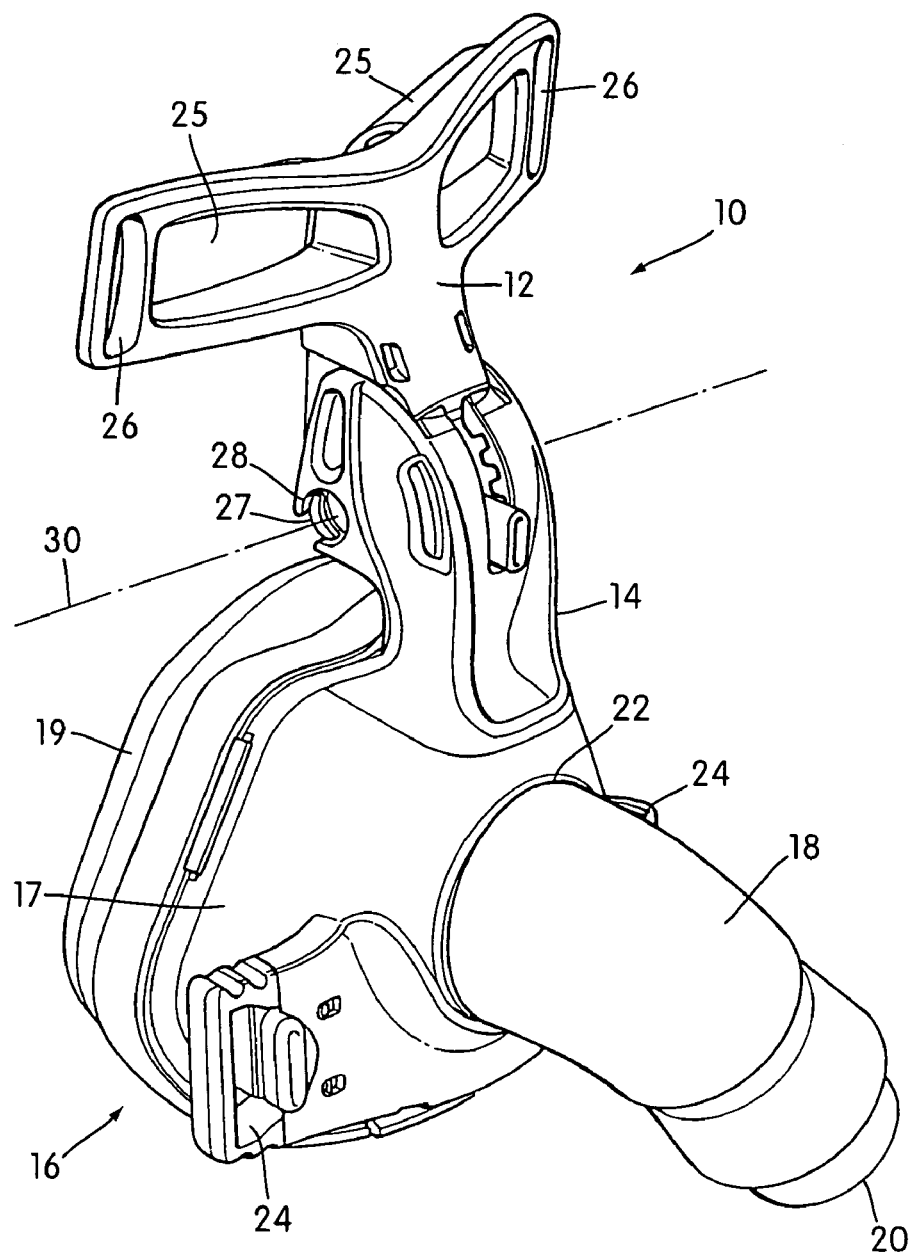
FIG. 1 is a front perspective view of a first embodiment of a forehead support according to the invention connected to a nasal mask.

FIG. 1 shows a first embodiment of a forehead support 10 according to the present invention. The forehead support 10 includes a generally T-shaped cushion frame 12 pivotally mounted to a joining member 14. The joining member 14 is connected to a nasal respiratory mask 16 used to supply breathable gas to a wearer's airways, as described in U.S. application Ser. No. 10/264,326, currently pending, and U.S. application Ser. No. 09/502,745, now U.S. Pat. No. 6,532,961, incorporated by reference in their entireties.

The mask 16 includes a mask shell 17 and a mask cushion 19. The mask shell 17 also includes an angled connector 18 which has a distal end 20 for connection to a gas supply conduit (not shown) and a proximal end 22 for connection to the mask 16. The connector 18 communicates the supplied gas from the gas supply conduit to the interior of the mask 16. The mask shell 17 also includes a pair of slotted connectors 24 to which are respectively connected ends of a lower head strap (not shown) for securing the nasal mask to the wearer's head.

The joining member 14 is connected on top of the mask shell 17 generally adjacent and above the wearer's nose. It will be appreciated that the nasal mask 16 shown is just one example of a respiratory mask that could be supported by the forehead support 10. For example, the forehead support also finds application in supporting full-face (i.e., nose and mouth) masks.

Forehead supports according to the invention can also be used with facial masks in which the gas supply connector 18 is incorporated into the mask in the general position of the joining member 14. In this type of mask, the supplied gas flows through or past the forehead support 10.

The T-shaped cushion frame 12 includes a pair of forehead cushions 25 mounted at each end of the upper portion of the T on the wearer contacting side. Examples of cushions 25 include open or closed cell foam, silicone, dual durometer foams, single pads or multiple pads joined together. The forehead cushions 25 can be integrally molded with the frame 12 or attached thereto by clips or adhesives or the like. The frame 12 also includes a slotted connector 26 adjacent each of the forehead cushions 25 to which are respectively connected ends of an upper head strap (not shown) for securing the cushion frame 12 to the wearer's head.

The T-shaped cushion frame 12 also includes a pair of shafts 27 (only one shown) on the lower portion of the T which are each respectively received in part circular openings 28 (only one shown) provided on the joining member 14. The shafts 27 can pivot or rotate in their respective openings 28 to provide for pivotal or rotational movement between the cushion frame 12 and the joining member 14 about axis 30 in the direction of double-headed arrow 31.

The curved shape of the cushions 25 allows them to effectively "roll" over the wearer's forehead during angular adjustment between the cushion frame 12 and the joining member 14.

Figure 3:
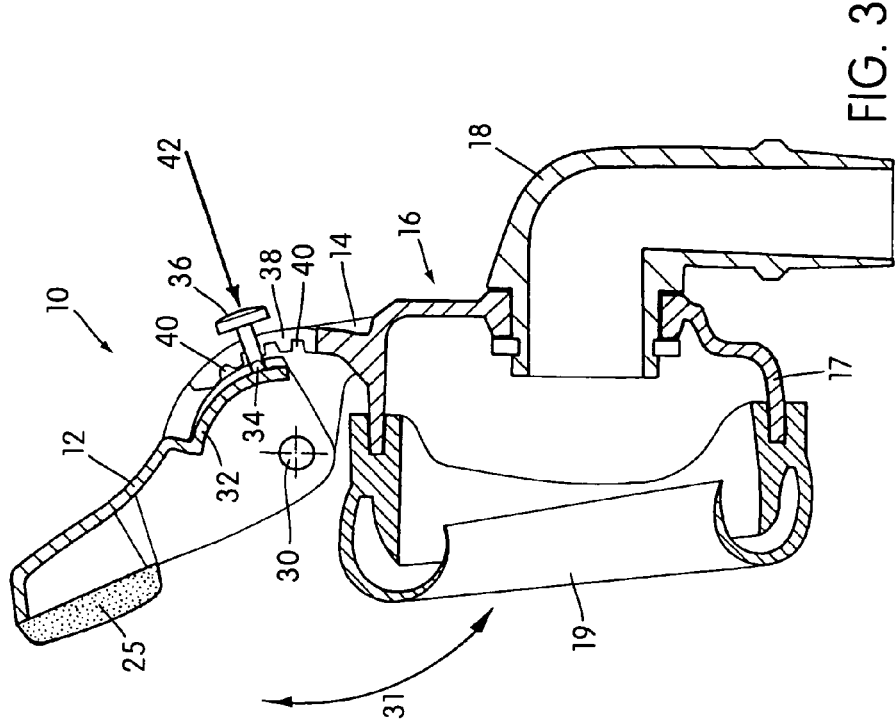
FIG. 3 is a cross sectional side view of the forehead support shown in FIG. 1 with the tongue of the cushion frame free of engagement with the pairs of grooves of the joining member.
Figure 2:
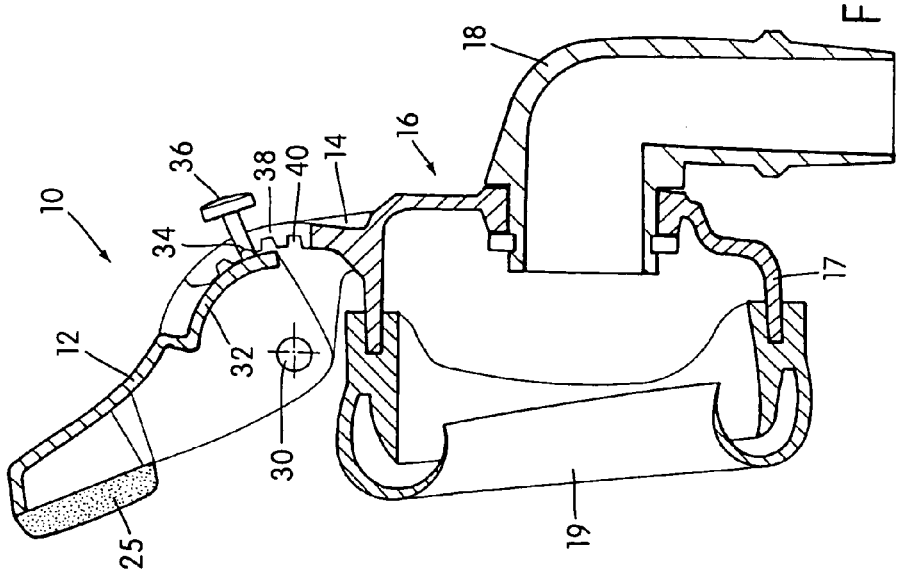
FIG. 2 is a cross sectional side view of the forehead support shown in FIG. 1 with the tongue of the cushion frame engaged with one of the pairs of grooves of the joining member.
Figure 4:
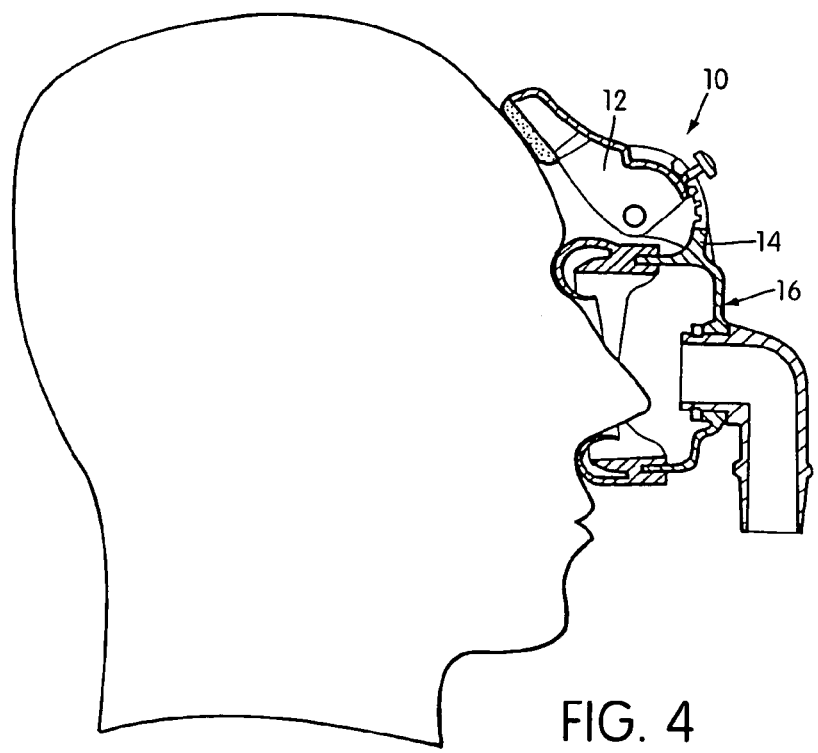
FIG. 4 is a cross sectional side view of the forehead support shown in FIG. 1 adjacent a wearer's head with the tongues and grooves engaged at the first of four positions.
Figure 5:
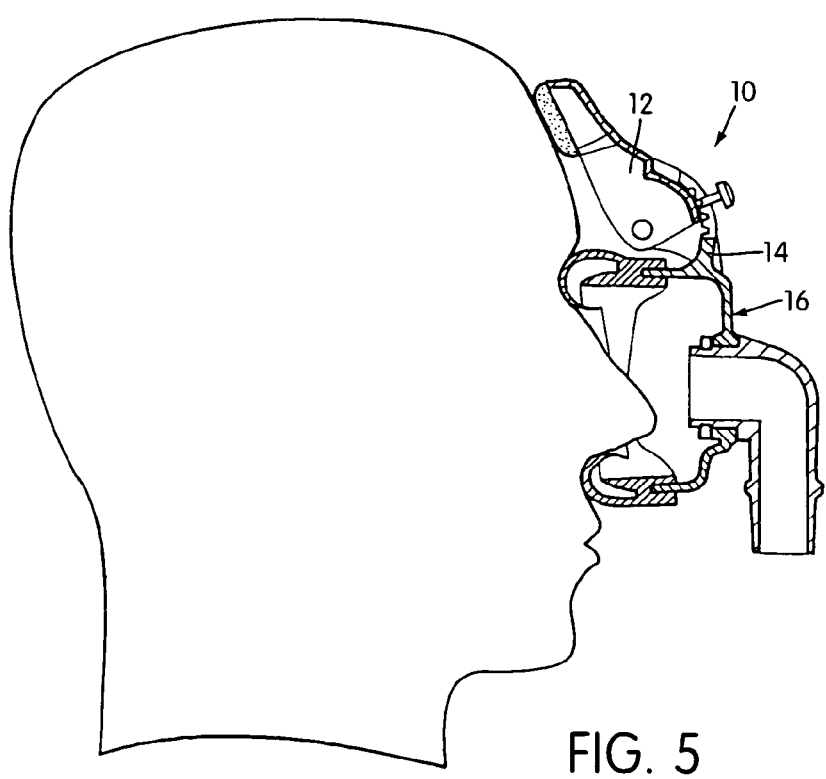
FIG. 5 is a cross sectional side view of the forehead support shown in FIG. 1 adjacent a wearer's head with the tongues and grooves engaged in the second of four positions.

As best shown in FIGS. 2 and 3, the cushion frame 12 also includes a flexible member 32 which has two side by side spaced apart tongues 34 and a middle protruding button 36 on its distal end. The joining member 14 also includes two generally arcuate shaped portions 38 that each have a pair of four grooves 40. It will be appreciated that the pair of four grooves is merely preferable and that only two or more grooves are required. It will also be appreciated that the flexible member 32 can be on the joining member 14 and the grooves 40 can be on the cushion frame 12. The tongue 34 and the grooves 40 extend in a direction substantially parallel to a line extending radially from the axis 30.

The cushion frame 12 is constructed from a plastics material, such as polypropylene or polycarbonate, which allows the member 32 to be flexed relative to the cushion frame 12 upon which is mounted when pressure is applied to the button 36 in the direction of arrow 42. The corresponding movement of the tongues 34 releases them from engagement with one of the pairs of grooves 40 (as shown in FIG. 3) to allow angular adjustment between the cushion frame 12 and the joining member 14 about the axis 30. Releasing the button 36 allows the tongue 34 to resiliently flex back towards the grooves 40. When the tongues 34 and one of the pairs of grooves 40 are aligned (as shown in FIGS. 2 and 4 to 7) the tongues 34 engage one of the pair of grooves 40. When the tongues 34 are engaged with one of the pair of grooves, the cushion frame 12 and joining member 14 are locked against pivotal movement therebetween at a predetermined angle.

FIGS. 4 to 7 respectively show forehead support 10 adjacent the heads of different wearers with the tongues 34 engaged in the first, second, third and fourth of the four pairs of grooves 40.

Figure 6:
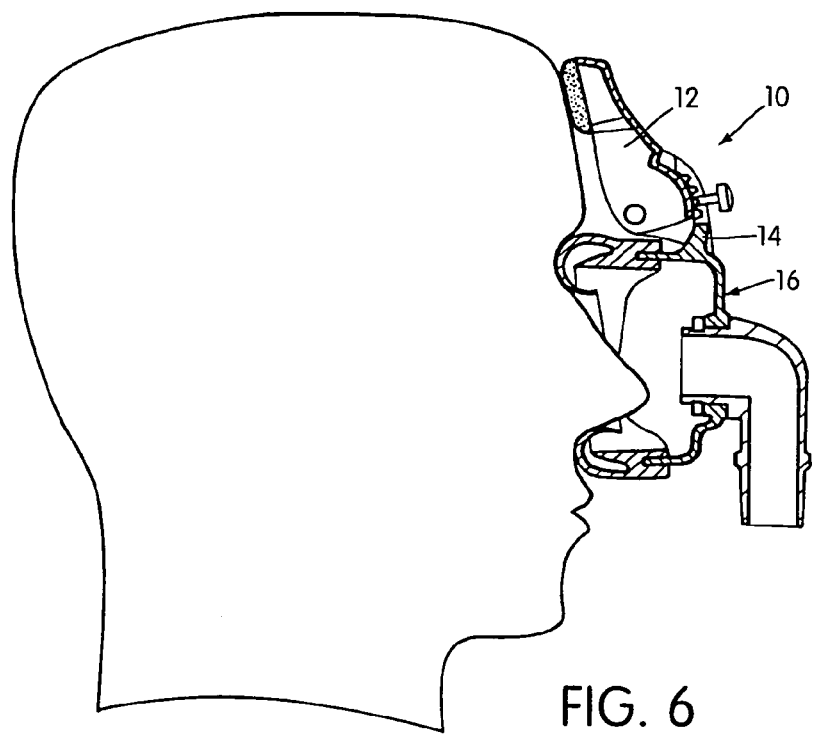
FIG. 6 is a cross sectional side view of the forehead support shown in FIG. 1 adjacent a wearer's head with the tongues and grooves engaged at the third of four positions.
Figure 7:
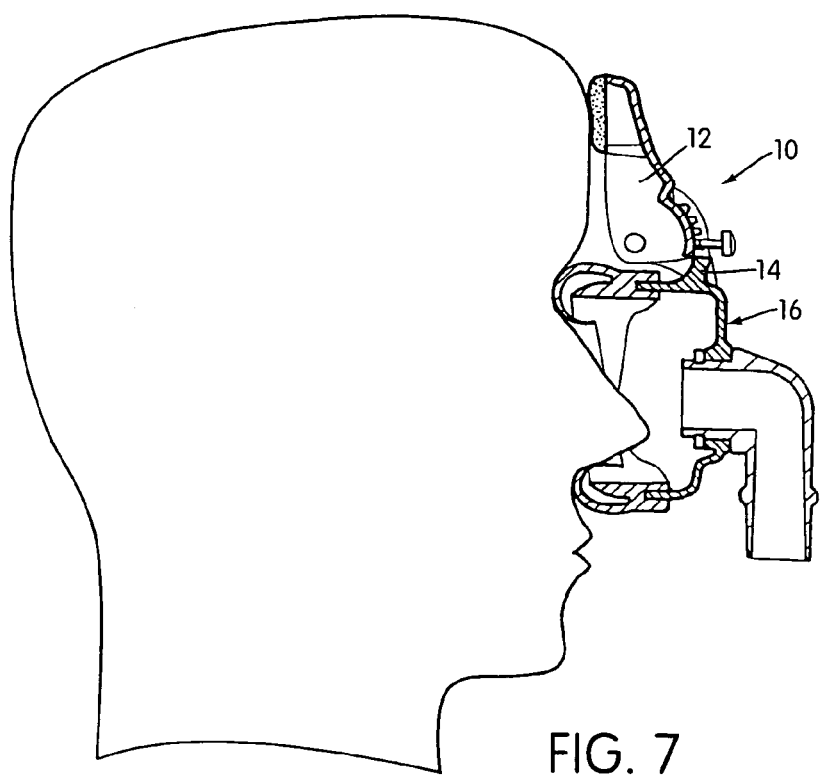
FIG. 7 is a cross sectional side view of the forehead support shown in FIG. 1 adjacent a wearer's head with the tongues and grooves engaged at the fourth of four positions.

As FIGS. 4 to 7 show, the angle between the cushion frame 12 and the joining member 14 adjacent the wearer's forehead can be increased to suit wearer's with relatively high nasal regions and relatively low foreheads (FIGS. 4 and 5) and decreased to suit wearers with relatively low nasal regions and relatively high foreheads (FIGS. 6 and 7).

In this way the forehead support 10 advantageously allows the mask 16 to be positioned to comfortably suit the particular topography of the wearer's face to ensure the mask cushion 19 is positioned ideally relative to the wearer's face. As examples, the relative position of the cushion frame 12 and the joining member 14 in FIG. 4 would be more suitable for use with a wearer having a shallow forehead or protruding cheeks or nose whilst the position of the cushion frame and joining member 14 in FIG. 7 would be more suitable for use with a wearers having a protruding or bulbous forehead.

Figure 8:
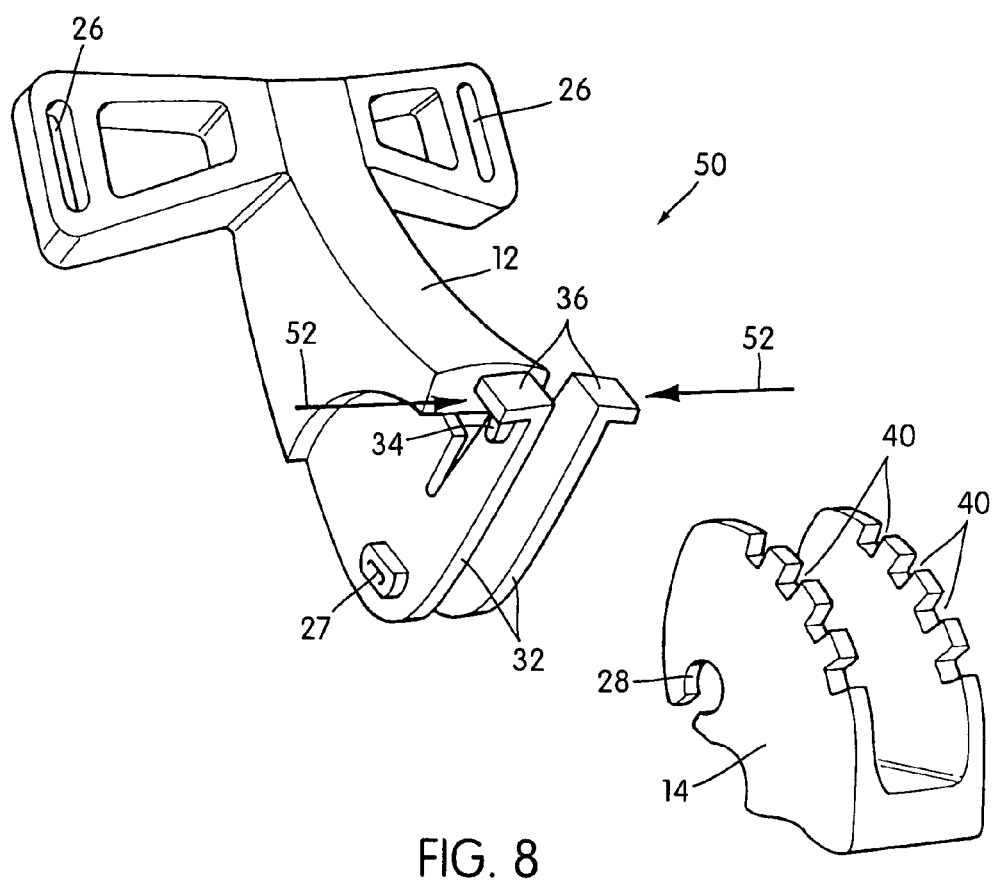
FIG. 8 is a partial exploded perspective view of a second embodiment of a forehead support according to the invention.
Figure 11:
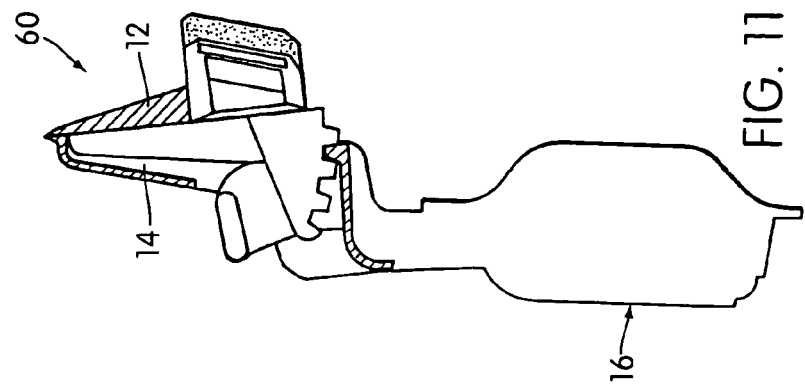
FIG. 11 is a cross sectional view of the forehead support shown in FIG. 9 with the tongue and grooves engaged at the second of four positions.
Figure 10:
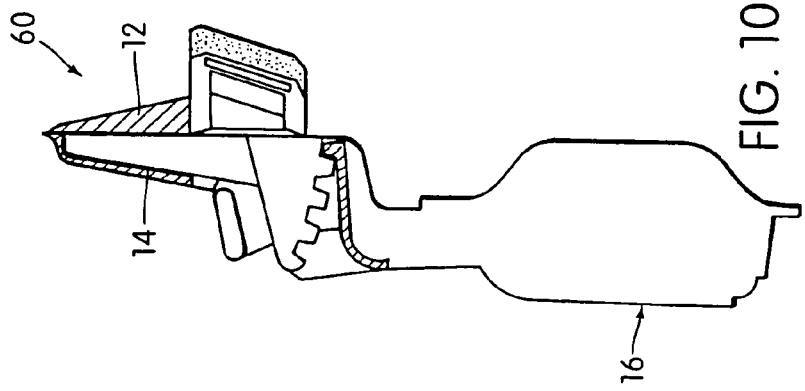
FIG. 10 is a cross sectional view of the forehead support shown in FIG. 9 with the tongue and grooves engaged at the first of four positions.

FIG. 8 shows a second embodiment of a forehead support 50 according to the present invention. Like reference numerals to those used in describing the first embodiment will be used to denote like features in relation to the second embodiment.

In the second embodiment, there are two buttons 36. Pressing the buttons together in the direction of arrows 52 flexes the tongues 34 towards each other to disengage them from the grooves 40 and allow angular adjustment between the cushion frame 12 and the joining member 14. Releasing the buttons 36 allows the tongues 34 to resiliently flex towards, and into engagement with, the grooves 40 to lock the cushion frame 12 and the joining member 14 against relative pivotal movement.

FIGS. 9 to 14 show a third embodiment of a forehead support 60 according to the present invention. Like reference to those used in describing the first embodiment will also be used to denote like features in relation to the third embodiment.

Figure 9:
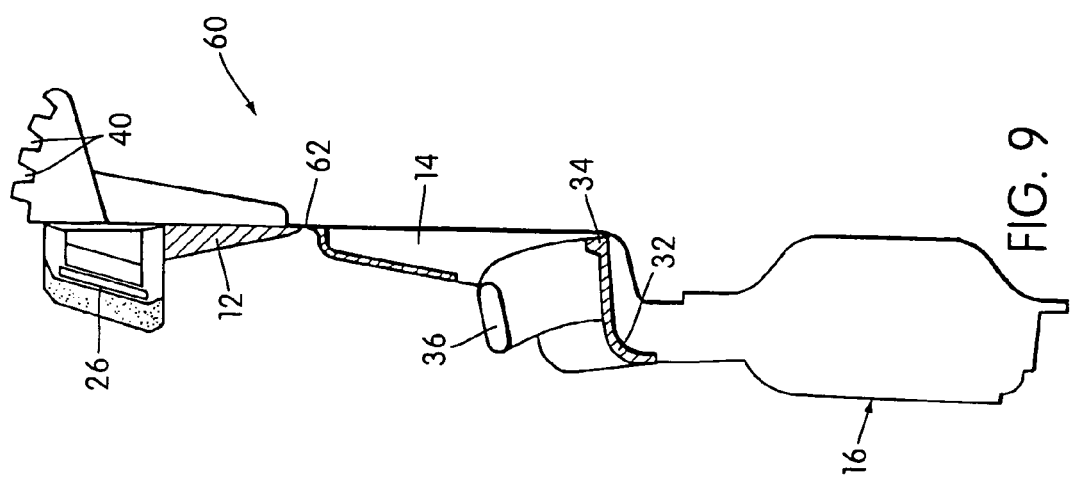
FIG. 9 is a cross sectional side view of a third embodiment of a forehead support according to the invention that includes an integrally formed cushion frame and joining member.

In the third embodiment, the cushion frame 12 is integrally molded with the joining member 14 and joined by an integral hinge 62 (sometimes known as a natural or living hinge). The cushion frame 12 and the joining member 14 can be pivoted relative to each other about the hinge 62. The forehead support 60 is molded in a substantially 'flat' configuration, as shown in FIG. 9. The cushion frame 12 is then pivoted through approximately 180° relative to the joining member 14 until the tongue 34 engages one of the four grooves 40. As with the earlier embodiments, pressing the button 36 in the direction of arrow 42 frees the tongue 34 from engagement with the grooves to allow adjustment of the angle between the cushion frame 12 and the joining member 14. The button 36 and the tongue 34 are inherently biased to a position engaging one of the grooves 40, again consistent with earlier embodiments.

In the preferred form shown, the mask shell 17 is also integrally formed with the joining member 14. This simplifies manufacturing and assembly and reduces production costs. The forehead support 60 is preferably manufactured from polypropylene due to its ability to mould integral hinges.

Figure 15:
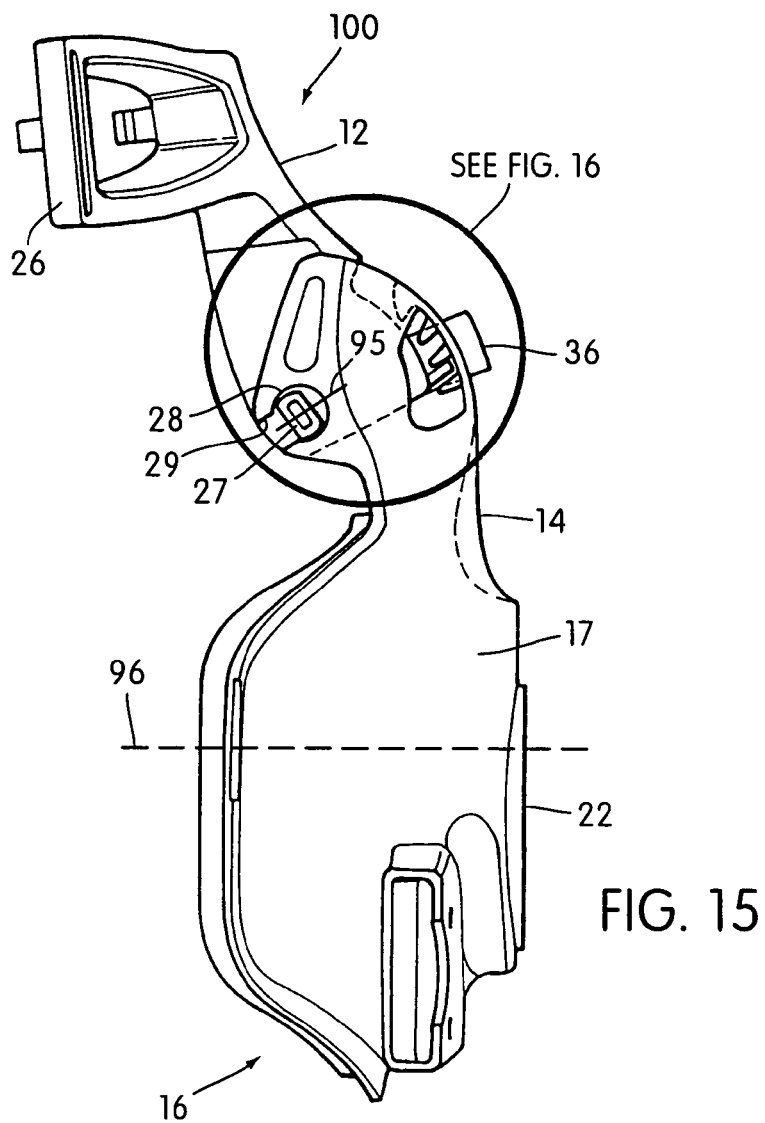
FIG. 15 is a side view of a fourth embodiment of a forehead support according to the invention.
Figure 16:
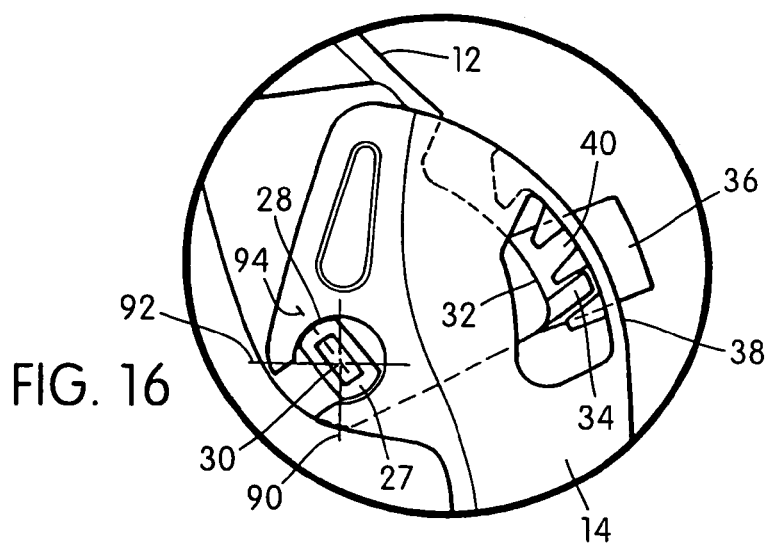
FIG. 16 is an enlarged detail view from FIG. 15.

FIGS. 15 and 16 show a fourth embodiment of a forehead support 100 according to the invention. Like reference to those used in describing the first embodiment will also be used to denote like features in relation to the fourth embodiment.

The fourth embodiment is almost identical to the first embodiment except the tongue 34 and the grooves 40 are angled with respect to a line extending radially from the axis 30 to the tongue 34 or the grooves 40. This angled arrangement reduces the likelihood that the tongue 34 will inadvertently release from engagement with one of the grooves 40 if the front of the mask 16 is subjected to a force in the direction of the wearer's face.

Although the invention has been described with reference to a specific example, it will be appreciated by those skilled in the art that the invention may be embodied in many other forms.

As an example, the forehead support can include means to resiliently bias the cushion frame and the joining member relative to one another such that they increase or decrease their angle relative to one another when the tongues are disengaged from one of the pairs of slots.

Figure 17:
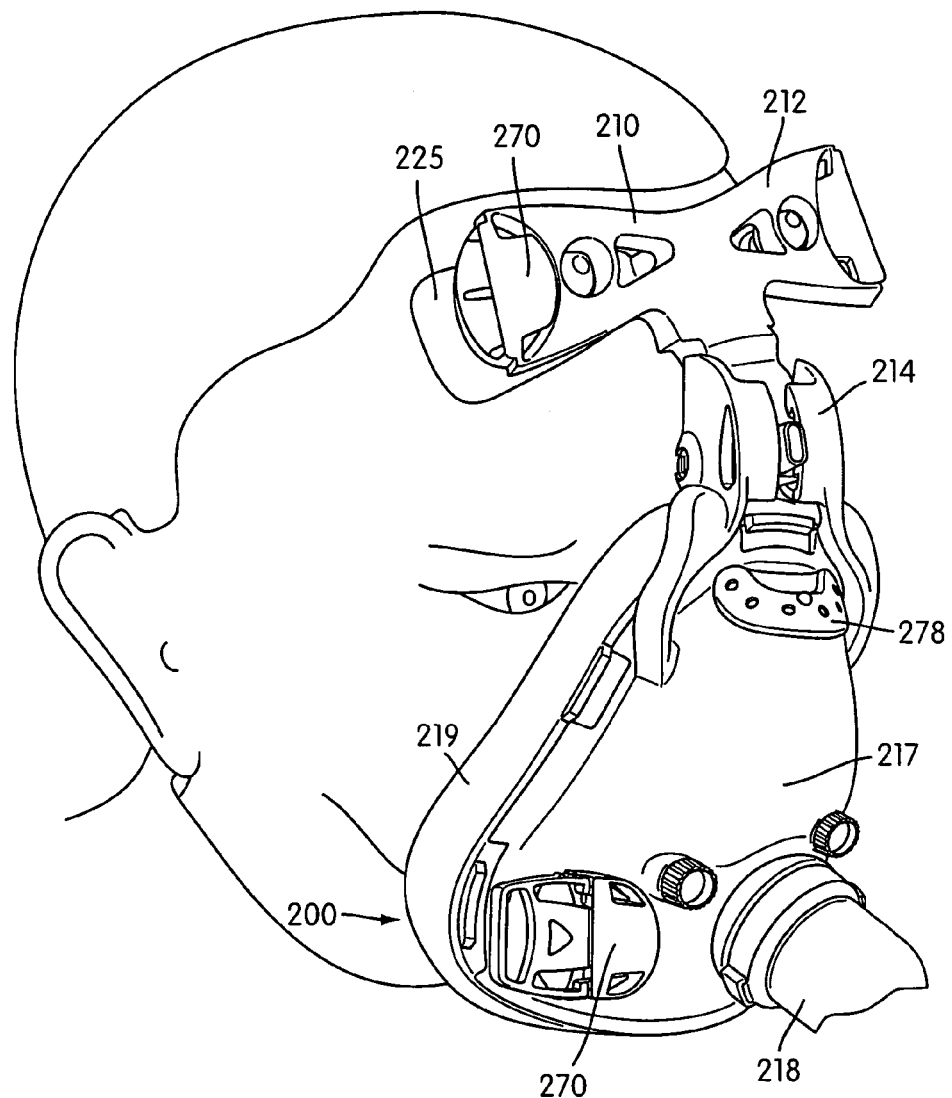
FIG. 17 is a perspective side view illustrating an embodiment of a full-face mask assembly having a forehead support engaged with a patient.
Figure 78:
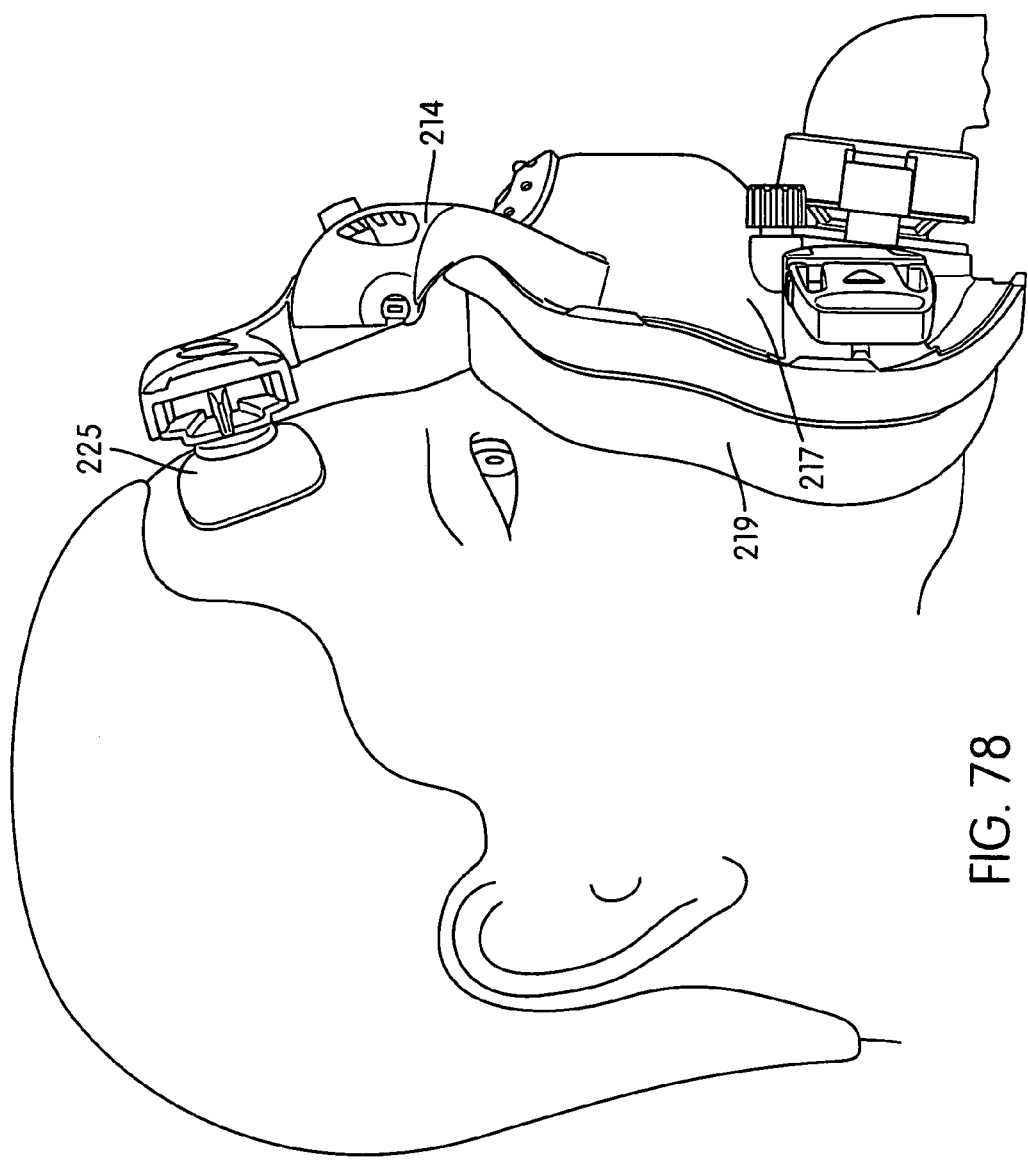
FIG. 78 is a side view of the full-face mask assembly shown in FIG. 17 engaged with a patient, the forehead support at a fourth of four positions.

FIGS. 17-78 illustrate another embodiment of a forehead support, indicated as 210, and a joining member, indicated as 214. As illustrated, the forehead support 210 and joining member 214 are structured for use with a full-face mask assembly 200. However, the forehead support 210 and joining member 214 may be structured for use with a nasal mask, for example.

Figure 18:
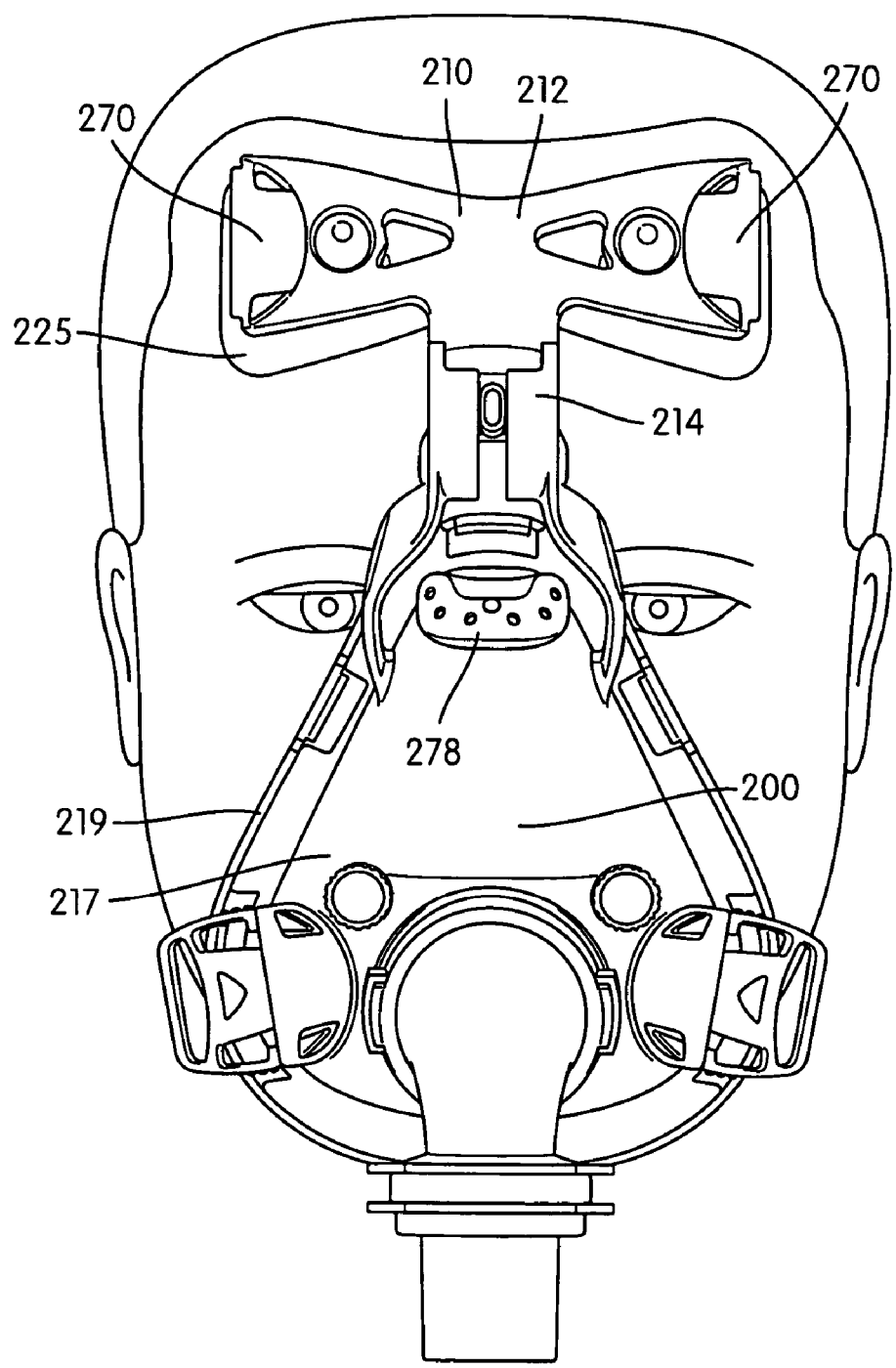
FIG. 18 is an enlarged front view of the full-face mask assembly shown in FIG. 17.
Figure 19:
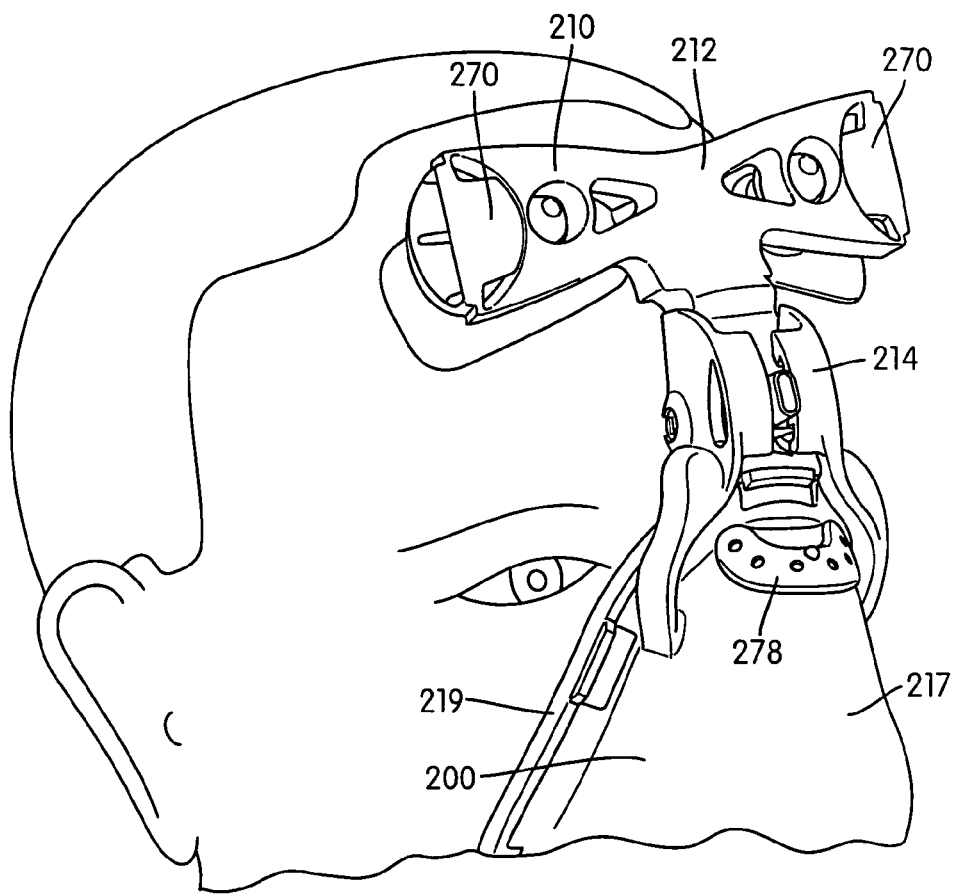
FIG. 19 is an enlarged side perspective view of the full-face mask assembly shown in FIG. 17.

As shown in FIGS. 17-19, the full-face mask assembly 200 includes a shell or frame 217 and a cushion 219 that may be permanently or removably connected to the frame 217 in any suitable manner. In the illustrated embodiment, the joining member 214 is integrally formed with an upper portion of the frame 217. The forehead support 210 is pivotally mounted to the joining member 214. A swivel elbow assembly 218 is removably attached to a front portion of the frame 217. The elbow assembly 218 is structured to be connected to a conduit that is connected to a pressurized supply.

A headgear assembly (not shown) can be removably attached to the frame 217 and forehead support 210 to maintain the mask assembly 200 in a desired adjusted position on the patient's face.

Figure 20:
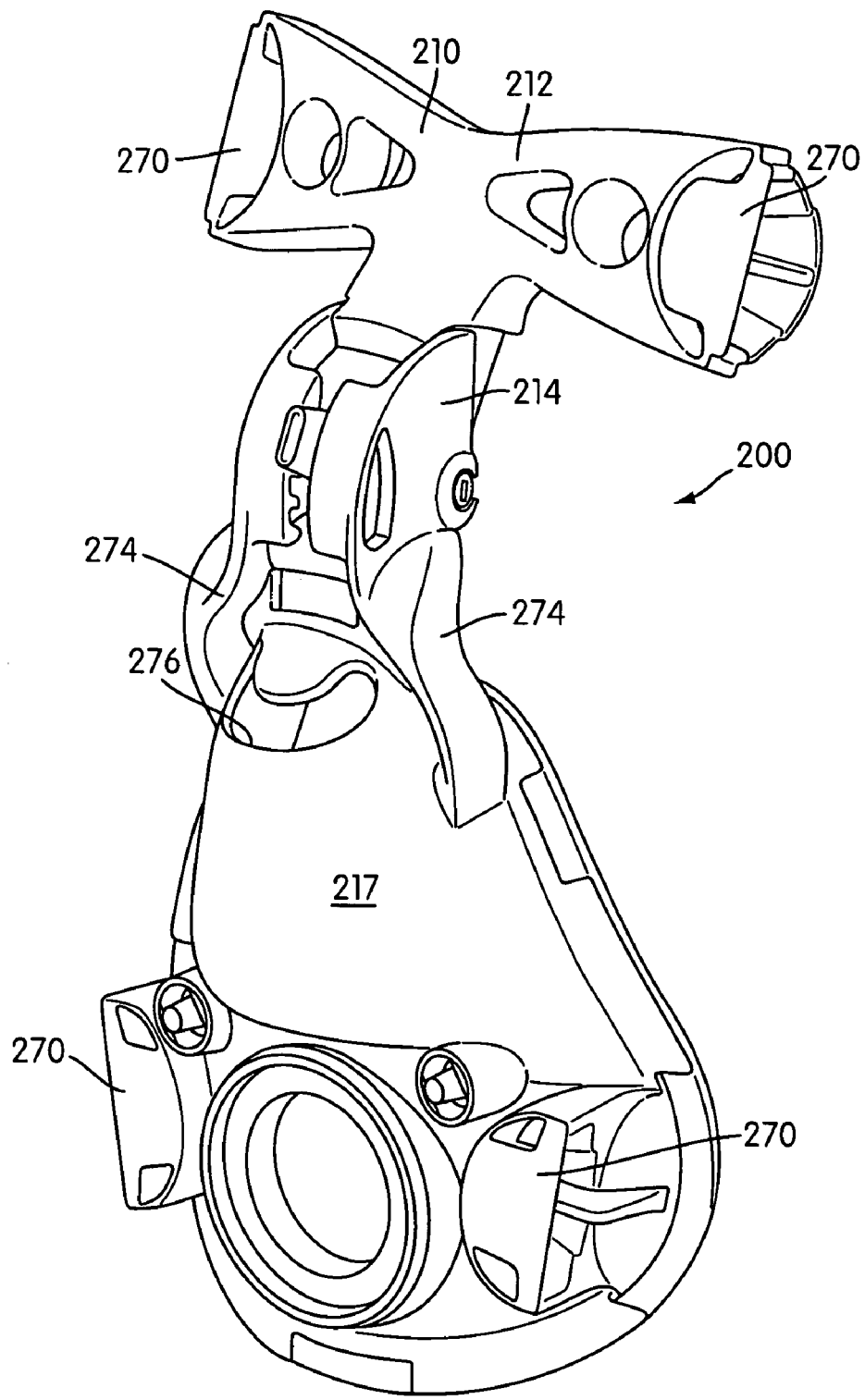
FIG. 20 is a perspective view of the frame and forehead support of the full-face mask assembly shown in FIG. 17.
Figure 20B:
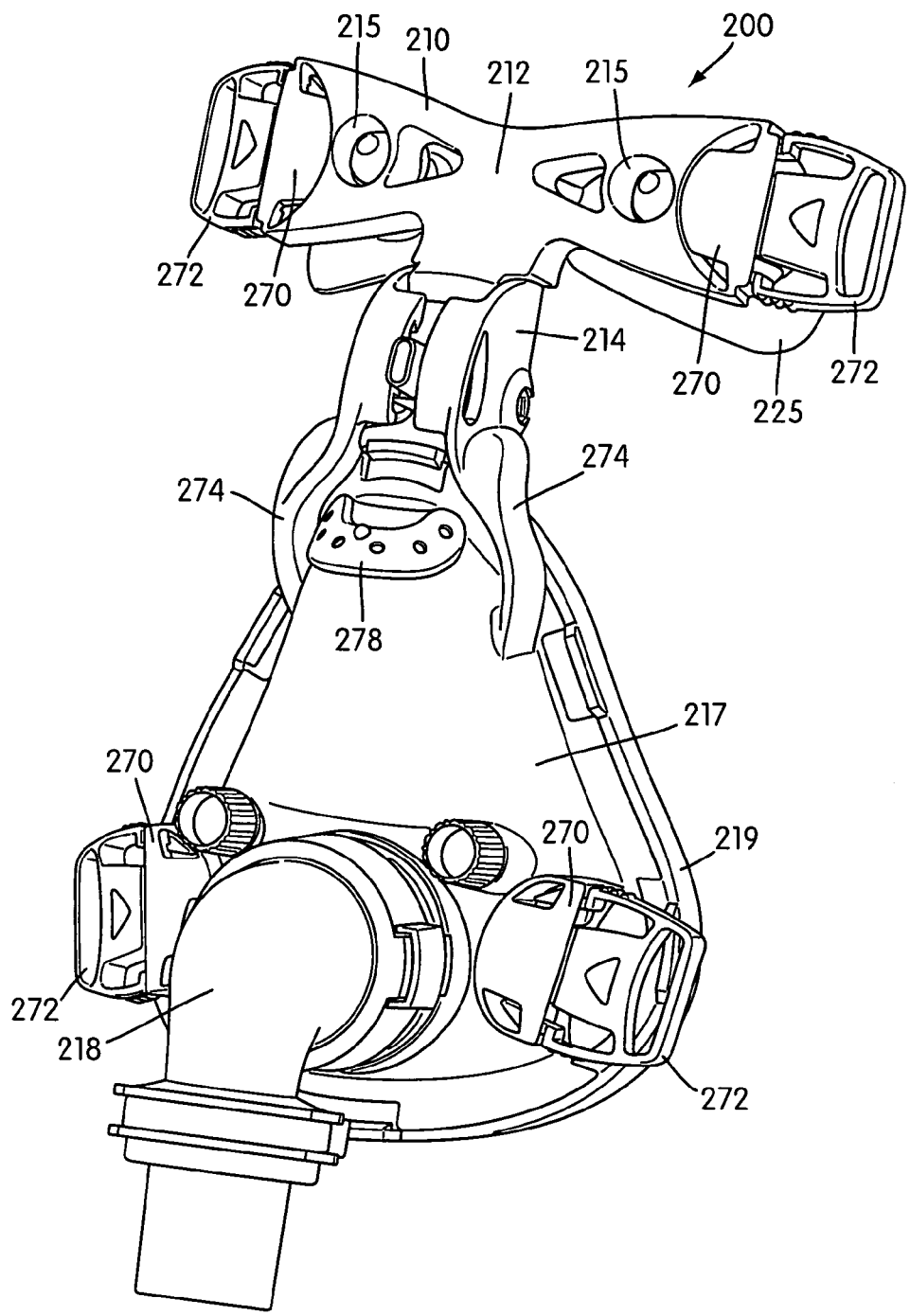
FIG. 20B is a perspective view of the full-face mask assembly shown in FIG. 17.
Figure 24:
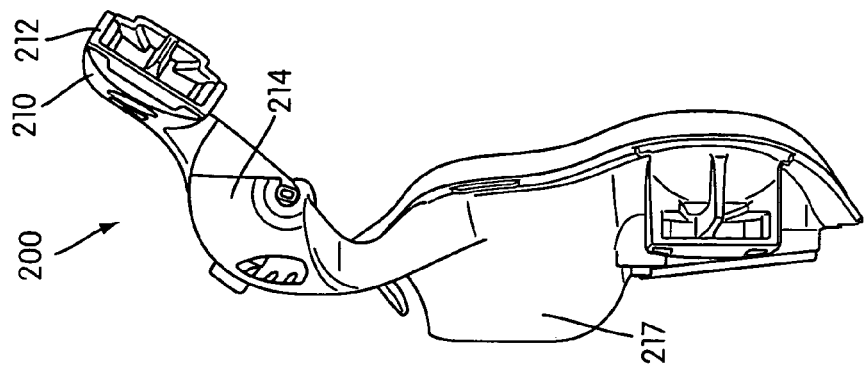
FIG. 24 is a side view of the frame and forehead support shown in FIG. 20 with the forehead support at a fourth of four positions.
Figure 23:
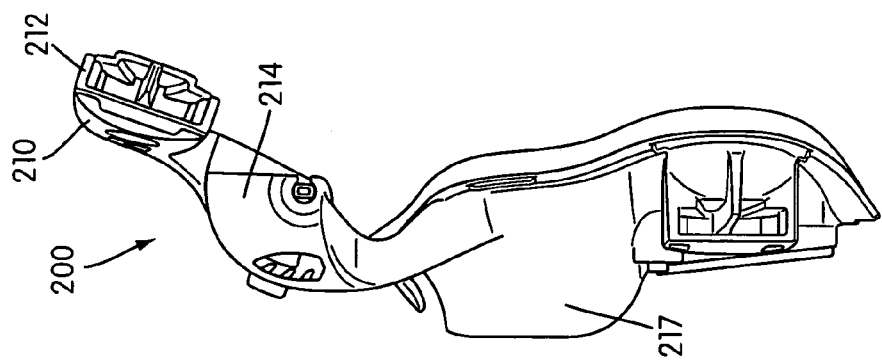
FIG. 23 is a side view of the frame and forehead support shown in FIG. 20 with the forehead support at a third of four positions.
Figure 22:
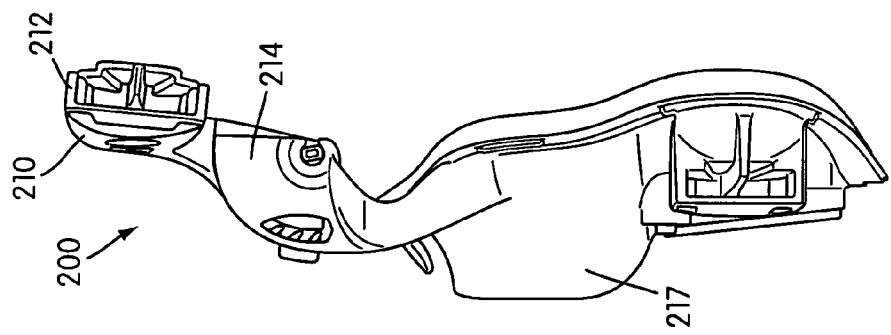
FIG. 22 is a side view of the frame and forehead support shown in FIG. 20 with the forehead support at a second of four positions.
Figure 21:
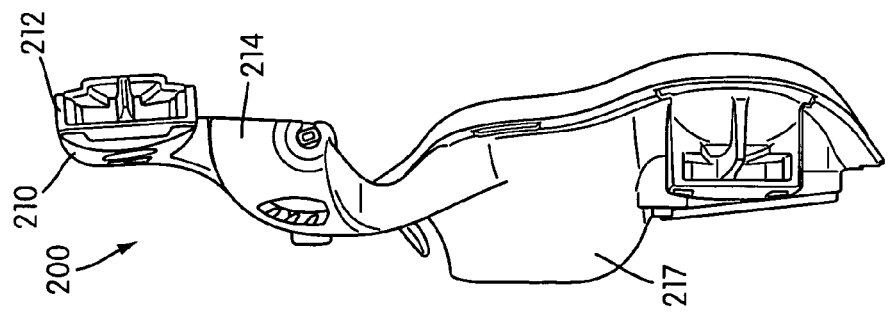
FIG. 21 is a side view of the frame and forehead support shown in FIG. 20 with the forehead support at one of four positions.
Figure 25:
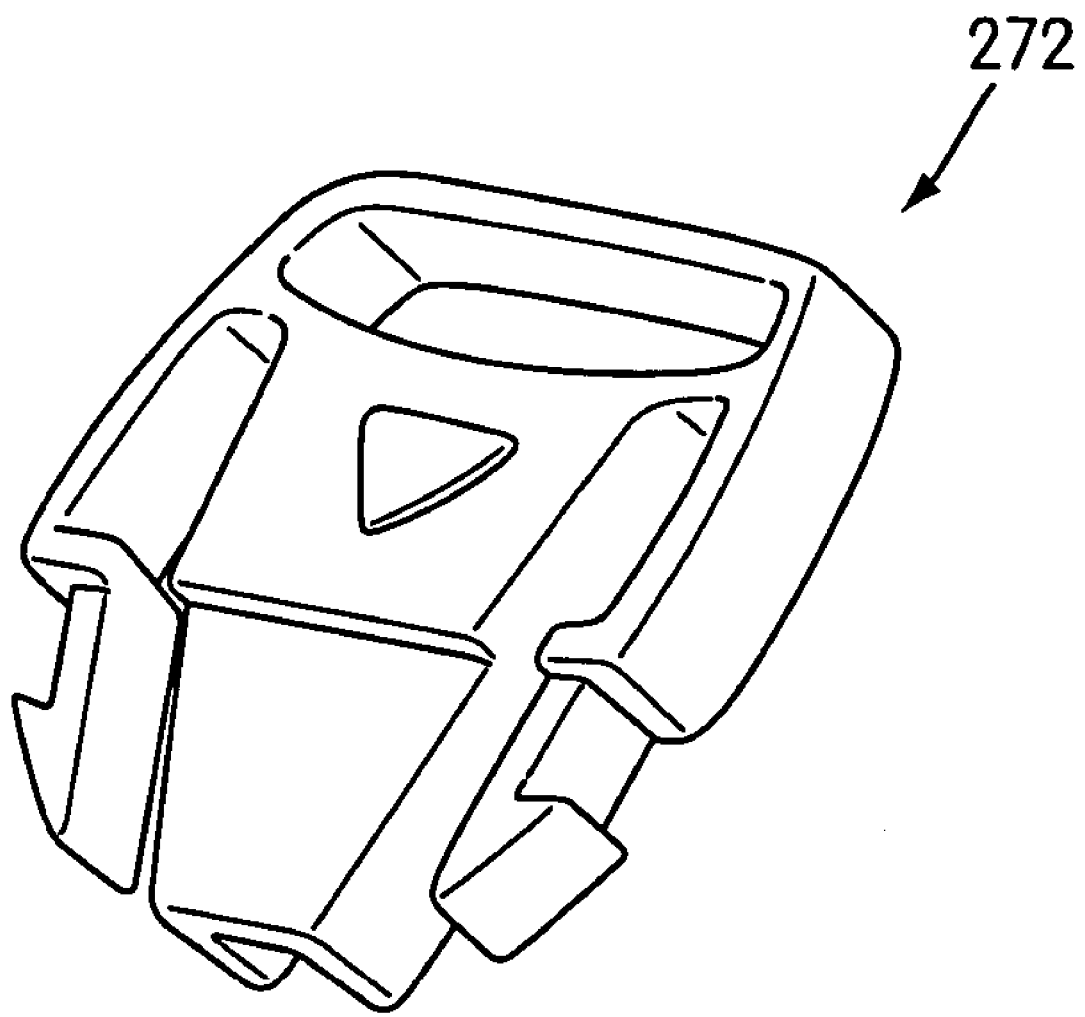
FIG. 25 is a perspective view of a locking clip for use with the frame and forehead support shown in FIG. 20.
Figure 26:
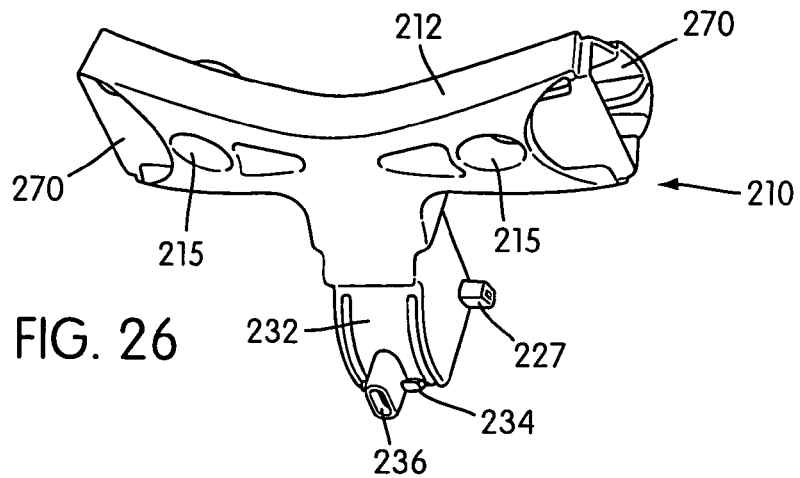
FIG. 26 is a top perspective view illustrating the forehead support shown in FIG. 20.
Figure 27:
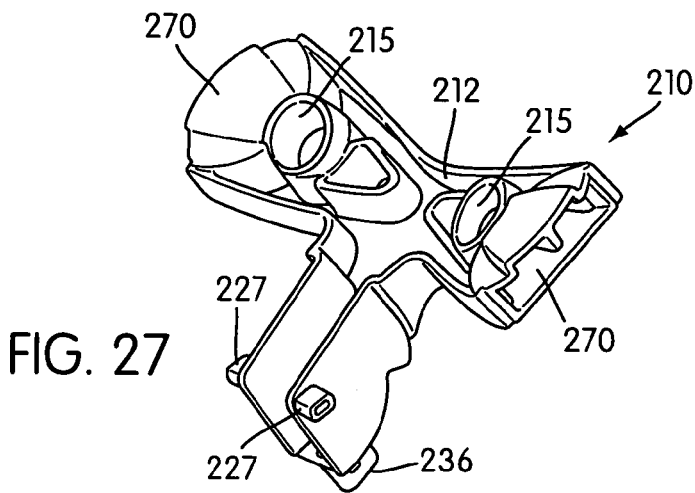
FIG. 27 is a rear perspective view of the forehead support shown in FIG. 26.
Figure 28:
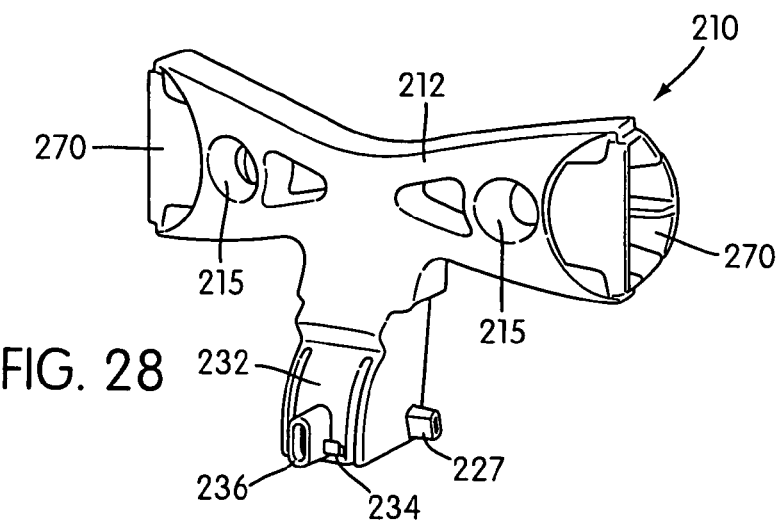
FIG. 28 is a front perspective view of the forehead support shown in FIG. 26.
Figure 29:
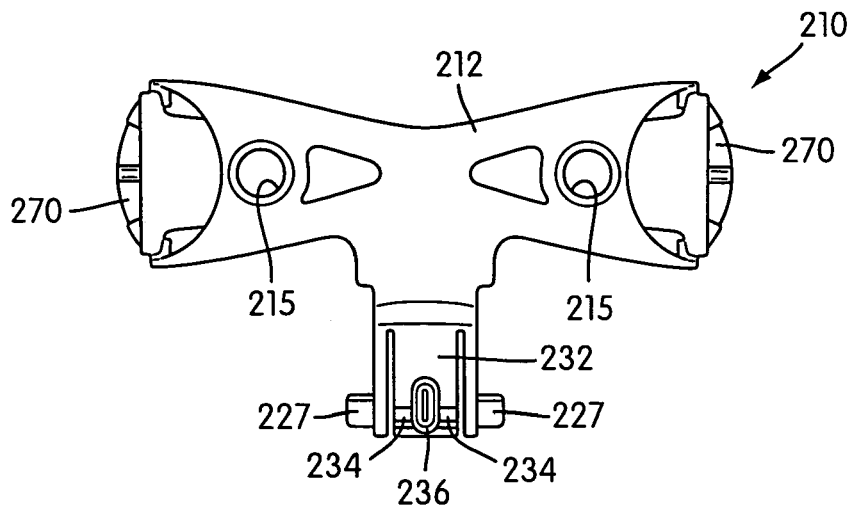
FIG. 29 is a front view of the forehead support shown in FIG. 26.

As shown in FIG. 20, each lateral side of the frame 217 includes a locking clip receiver assembly 270 structured to interlock with a locking clip 272 (see FIG. 25). As shown in FIG. 20, each lateral side of the forehead support 210 includes a locking clip receiver assembly 270 structured to interlock with a locking clip 272. Thus, four locking clips 272 are used, two locking clips 272 for the frame 217 and two locking clips 272 for the forehead support 210. FIG. 20B illustrates locking clips 272 engaged with locking clip receiver assemblies 270 provided on the frame 217 and forehead support 210. In use, upper straps of the headgear assembly would be removably connected to locking clips 272 for the forehead support 210 and lower straps of the headgear assembly would be removably connected to locking clips 272 for the frame 217.

Further details of embodiments of structure and operation of locking clip receiver assemblies 270 and locking clips 272 are disclosed in the U.S. patent application Ser. No. 10/655,603 to Lithgow et al., filed Sept. 5, 2003, the entirety of which is herein incorporated by reference.

Figure 32:
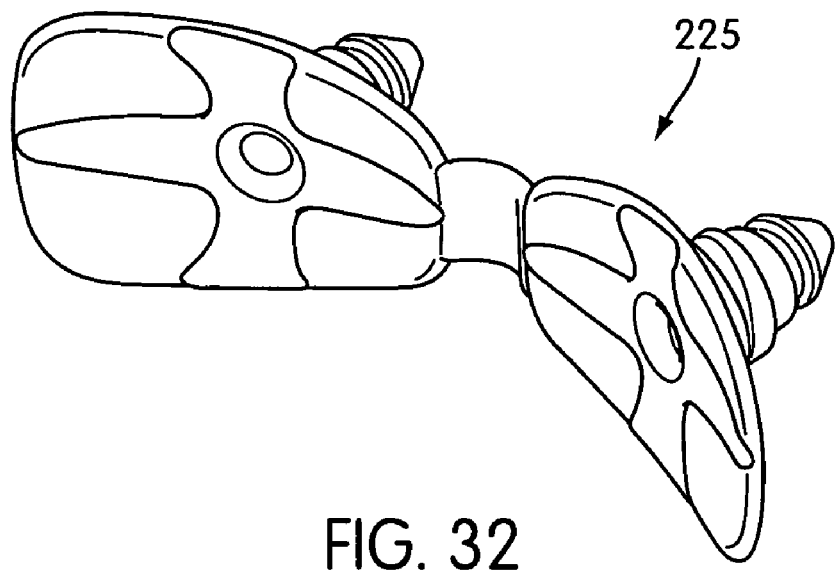
FIG. 32 is a rear perspective view of an embodiment of a forehead cushion for use with the forehead support shown in FIG. 20.
Figure 33:
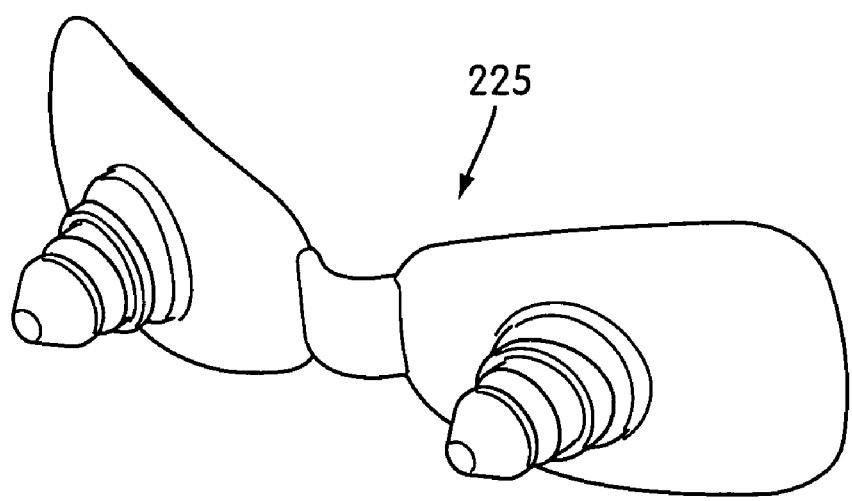
FIG. 33 is a front perspective view of the forehead cushion shown in FIG. 32.
Figure 34:
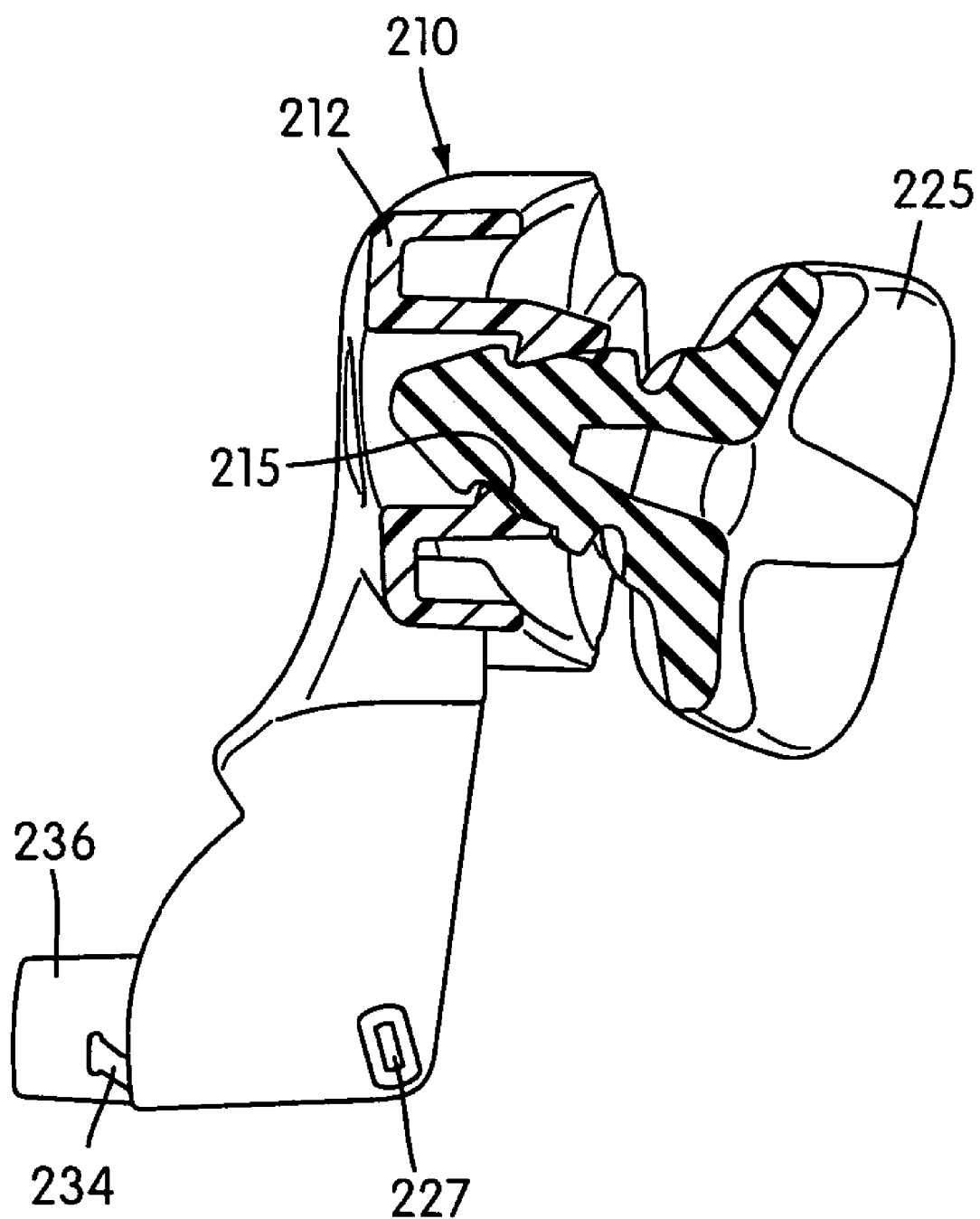
FIG. 34 is a cross-sectional view illustrating the forehead cushion shown in FIG. 32 secured to the forehead support shown in FIG. 20.
Figure 35:
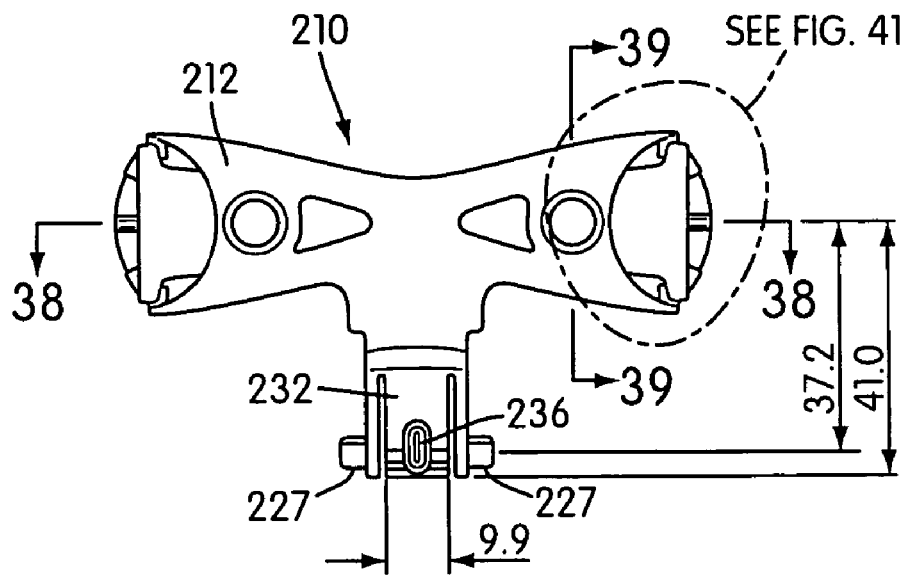
FIG. 35 is a front view illustrating an embodiment of a forehead support.
Figure 36:
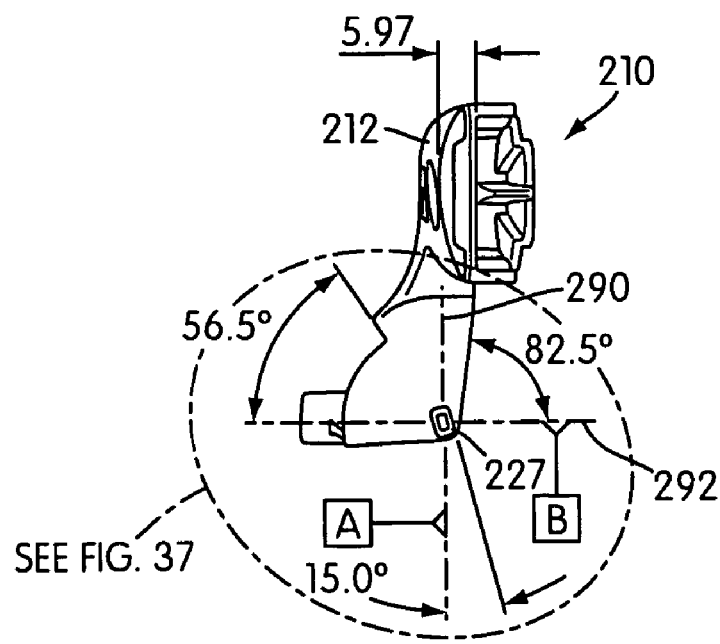
FIG. 36 is a side view of the forehead support shown in FIG. 35.
Figure 37:
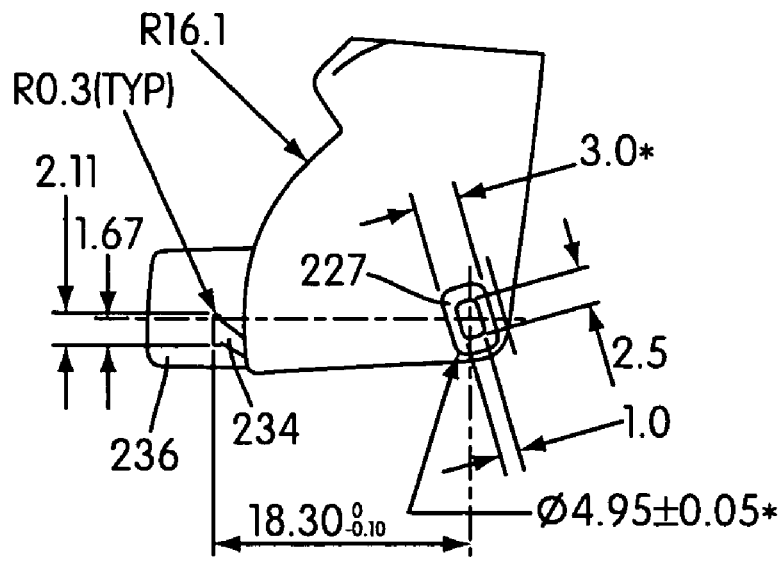
FIG. 37 is an enlarged view of FIG. 36.
Figure 38:
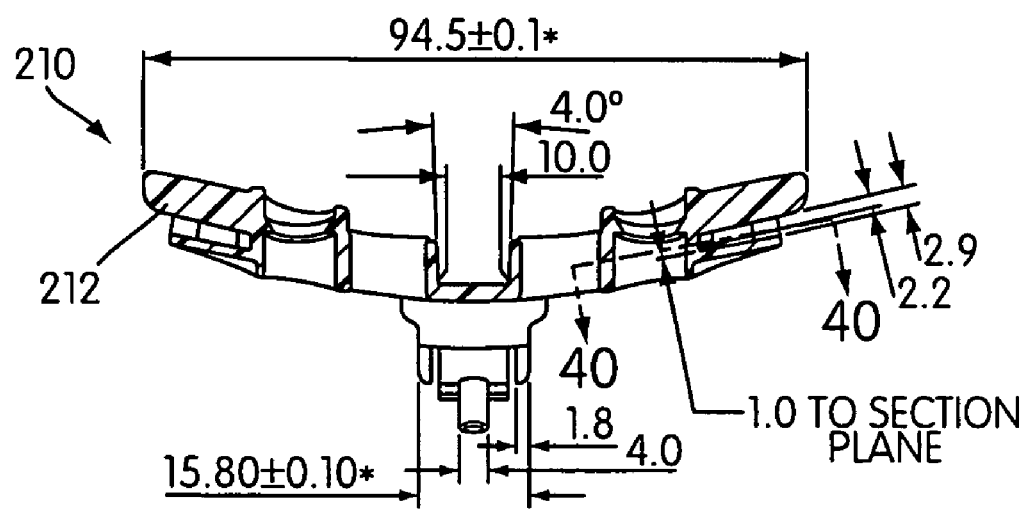
FIG. 38 is a cross-section taken along line 38-38 of FIG. 35.
Figure 39:
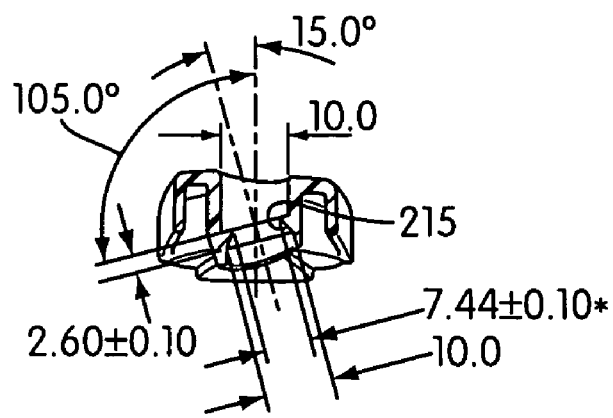
FIG. 39 is a cross-section taken along line 39-39 of FIG. 35.
Figure 40:
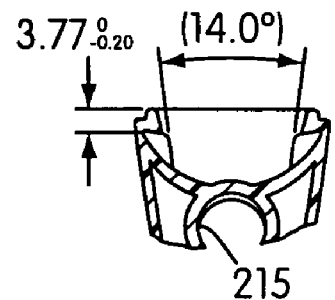
FIG. 40 is a cross-section taken along line 40-40 of FIG. 38.
Figure 41:
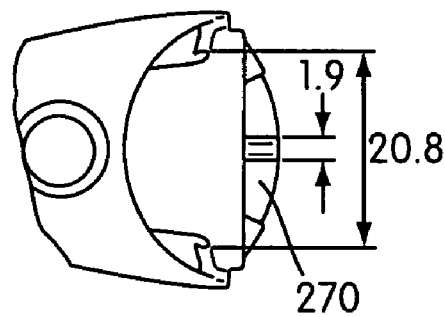
FIG. 41 is an enlarged view of FIG. 35.
Figure 42:
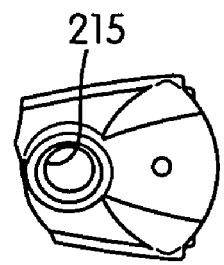
FIG. 42 is a back view of a portion of the forehead support shown in FIG. 35.
Figure 73:
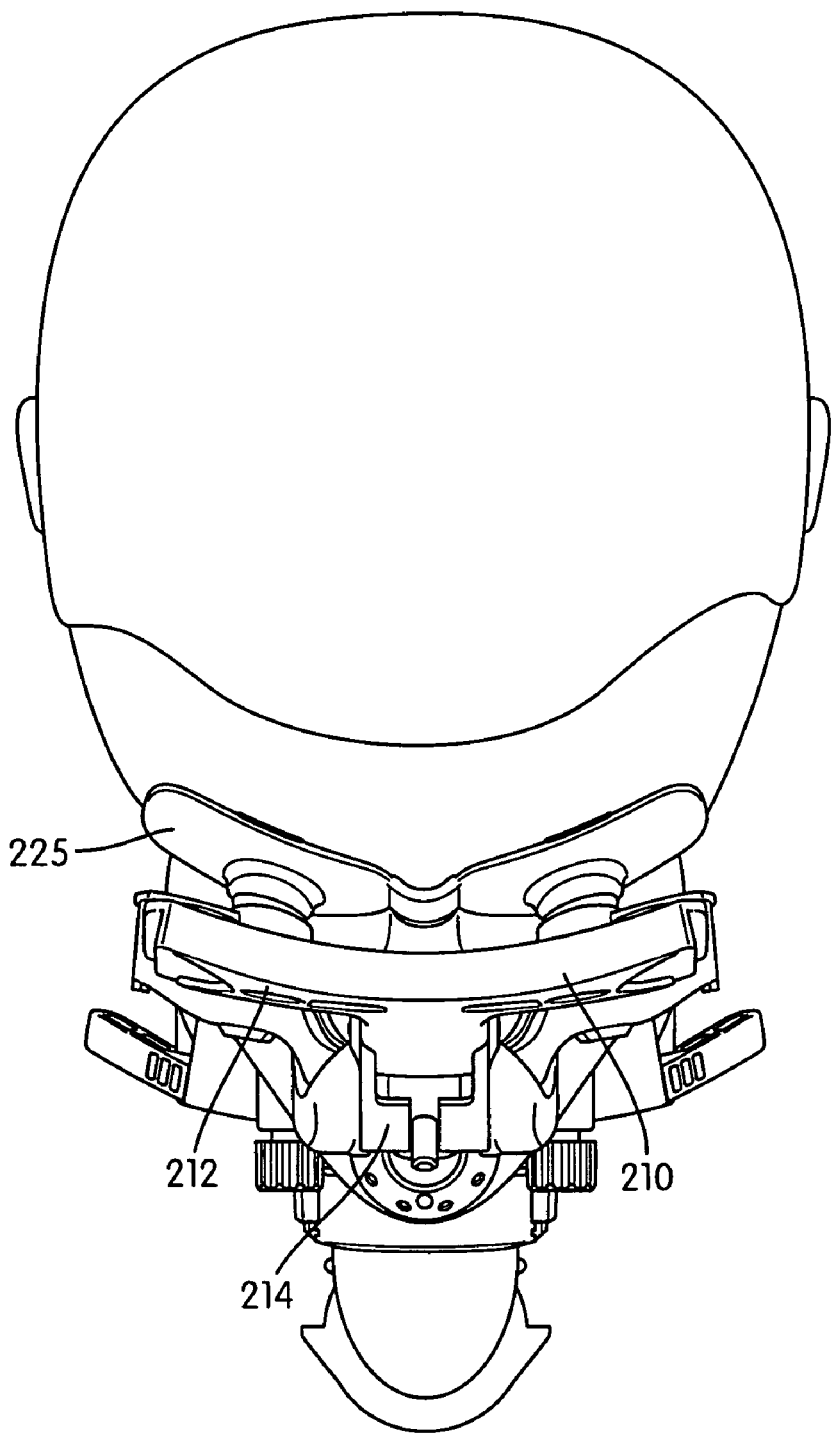
FIG. 73 is a top view illustrating the full-face mask assembly shown in FIG. 17 engaged with a patient.
Figure 74:
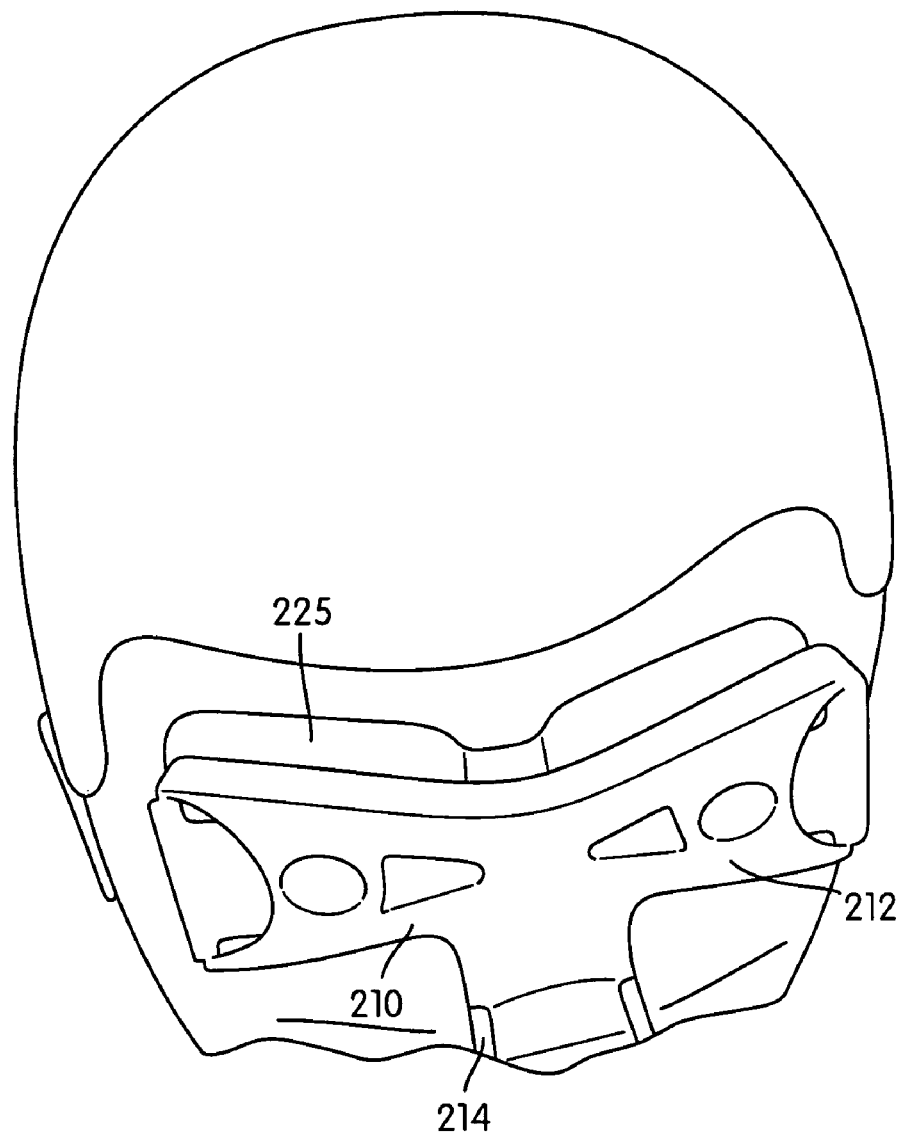
FIG. 74 is a front view illustrating the full-face mask assembly shown in FIG. 17 engaged with a patient.
Figure 75:
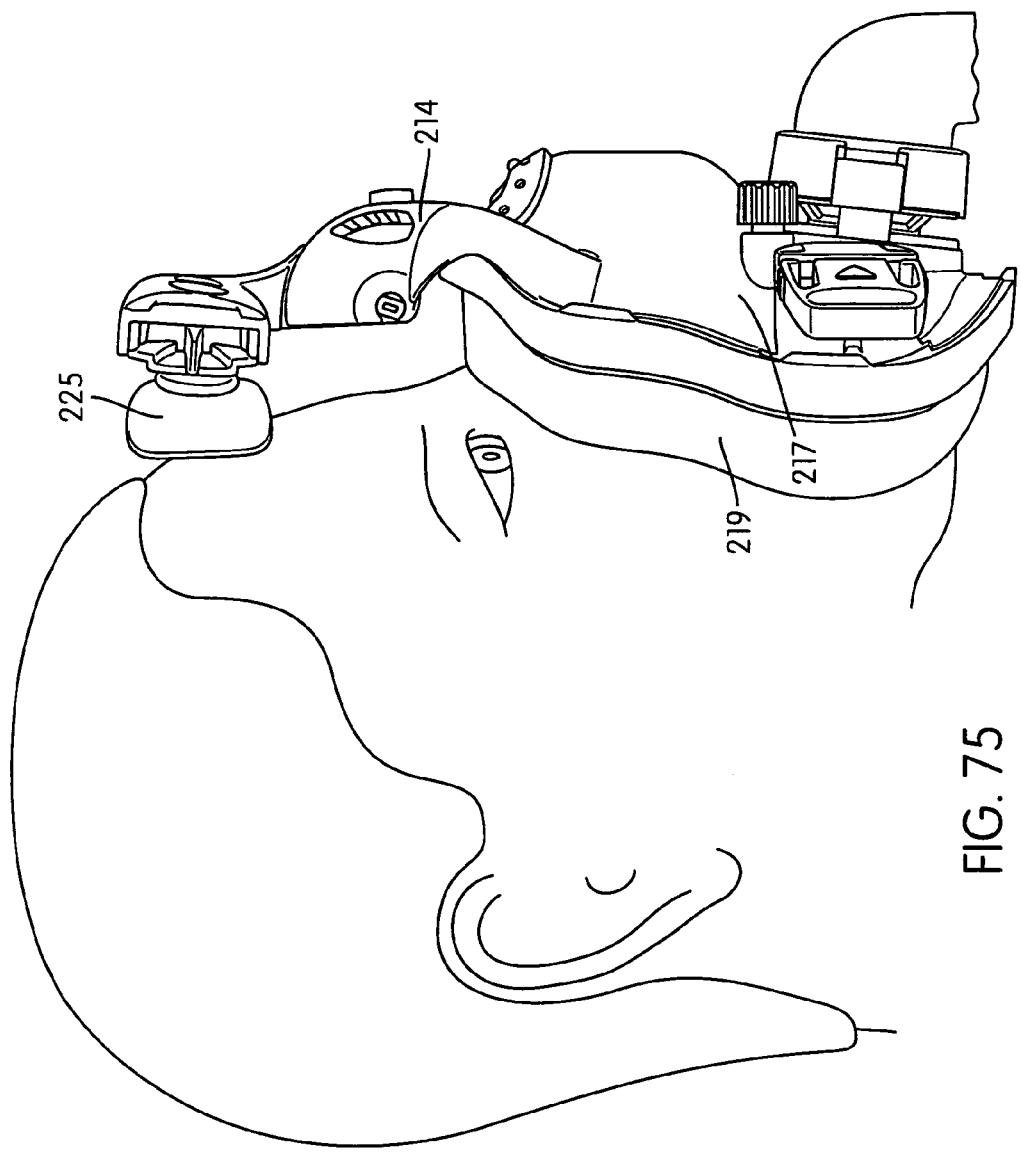
FIG. 75 is a side view of the full-face mask assembly shown in FIG. 17 engaged with a patient, the forehead support at one of four positions.
Figure 76:
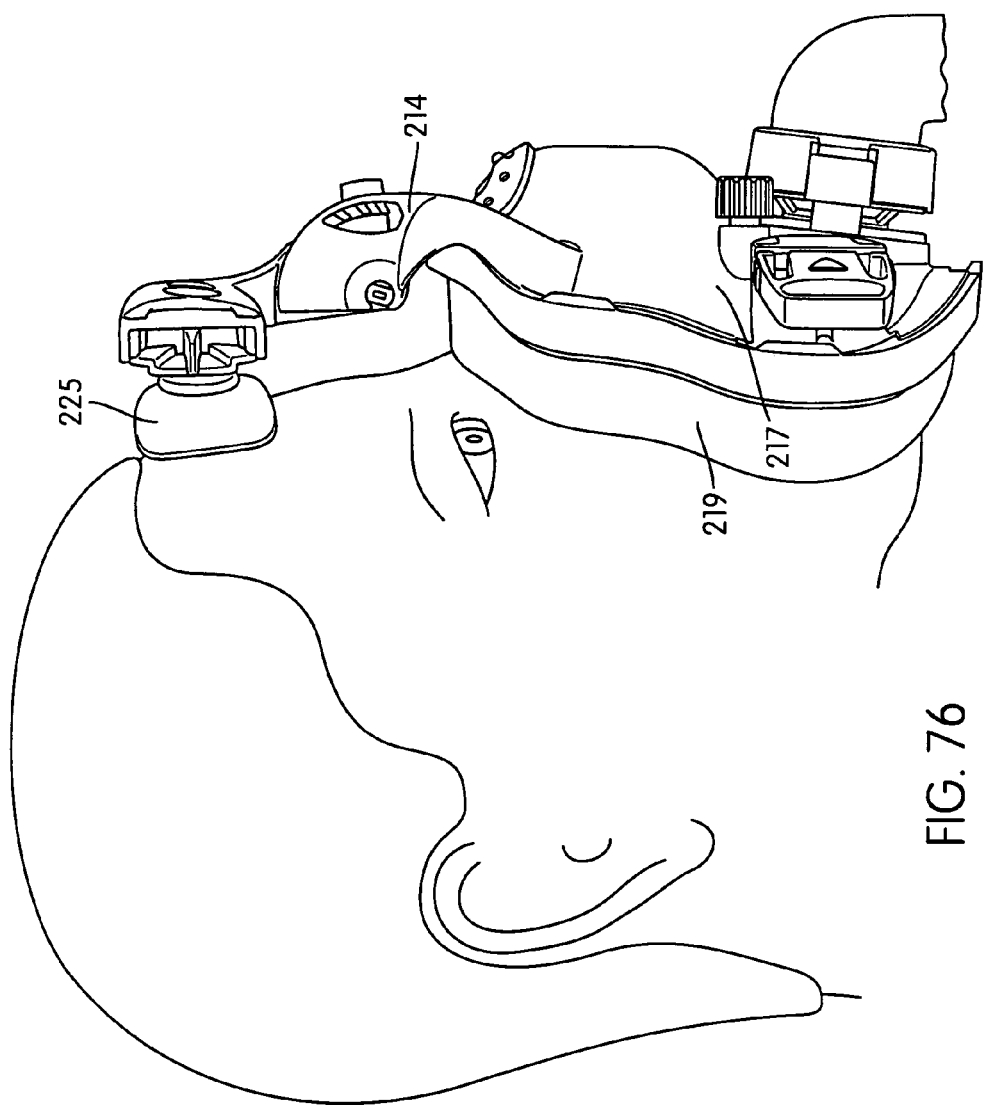
FIG. 76 is a side view of the full-face mask assembly shown in FIG. 17 engaged with a patient, the forehead support at a second of four positions.

As shown in FIGS. 26-30, the forehead support 210 includes a generally T-shaped cushion frame 212. Each end of the upper portion of the T-shape includes an opening 215 adapted to secure a forehead cushion 225 (see FIGS. 32 and 33). As shown in FIG. 34, the openings 215 are angled downwardly so as to properly orient the forehead cushion 225 with respect to patient's forehead. For example, FIGS. 73-74 illustrate the forehead cushion 225 engaged with the patient's forehead. Also, FIGS. 75-78 illustrate the forehead cushion 225 engaged with the patient's forehead at different positions of the forehead support 210. As illustrated, the forehead cushion 225 is angled so as to be in a suitable position to engage the patient's forehead. Also, the forehead cushion 225 is structured to allow relative movement of the forehead cushion 225 with respect to the forehead support 210 to improve patient comfort.

Further details of embodiments of structure and operation of the forehead cushion 225 is disclosed in the U.S. patent application Ser. No. 10/655,595 to Lang et al., filed Sept. 5, 2003, the entirety of which is herein incorporated by reference.

As shown in FIGS. 26-31, the T-shaped cushion frame 212 includes a pair of shafts 227 on the lower portion of the T-shape which are each respectively received in openings 228 provided on the joining member 214. In contrast to the shafts 27 of T-shaped cushion frame 12 in FIG. 16, the shafts 227 of T-shaped cushion frame 212 have a smaller shape and different angle.

Specifically, the shafts 27 and the shafts 227 may have a generally non-circular, e.g., rectangular shape, defining a major longitudinal axis. The diameter and width of the shafts 227 are smaller than the diameter and width of the shafts 27.

Figure 30:
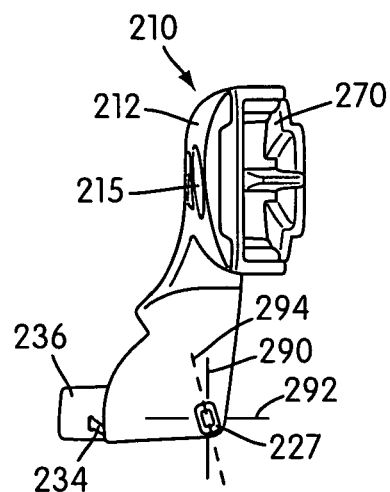
FIG. 30 is a side view of the forehead support shown in FIG. 26.
Figure 31:
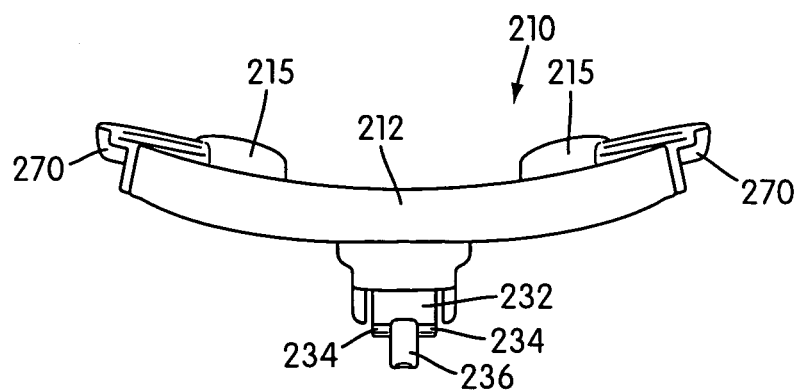
FIG. 31 is a top view of the forehead support shown in FIG. 26.

Also, as shown in FIG. 16, the cushion frame 12 has a vertical axis 90 and a horizontal axis 92. The longitudinal edges of the shafts 27 define a longitudinal axis 94 of the shafts 27 therebetween. If the portion of the cushion frame 12 facing toward the patient is considered the rear portion of the cushion frame 12 and the portion of the frame 12 facing outwardly from the patient is considered the front portion of the cushion frame 12, the shafts 27 are angled rearward of the vertical axis 90 of the cushion frame 12, i.e., angled toward the rear portion of the cushion frame 12. As shown in FIG. 30, the cushion frame 212 has a vertical axis 290 and a horizontal axis 292. The longitudinal edges of the shafts 227 define a longitudinal axis 294 of the shafts 227 therebetween. In contrast to shafts 27, if the portion of the cushion frame 212 facing toward the patient is considered the rear portion of the cushion frame 212 and the portion of the frame 212 facing outwardly from the patient is considered the front portion of the cushion frame 212, the shafts 227 are angled forward of the vertical axis 90 of the cushion frame 12, i.e., angled toward the front portion of the cushion frame 212.

This change in shape and geometry of the shafts 227 facilitates assembly of the forehead support 210 to the joining member 214 and provides more clearance of the forehead support 210 from the patient's forehead, as will be further discussed.

The cushion frame 212 also includes a flexible member 232 which has two side by side spaced apart tongues 234 and a middle protruding button 236 on its distal end.

FIGS. 35-42 show further structural details and various dimensions in one embodiment of the forehead support 210. For example, the shafts 227 of the forehead support 210 has a diameter of about 5 mm and a width of about 3 mm. Also, the shafts 227 are angled about 15° forward of the vertical axis 290 of the cushion frame 212 (as viewed in FIG. 36). In the embodiment of forehead cushion 210, the dimensions illustrated in FIGS. 35-42 may vary ±10%.

FIGS. 43-48 illustrate an embodiment of the frame 217 including joining member 214. As illustrated, the joining member 214 includes two generally arcuate shaped portions 238 that each have four grooves 240. It should be appreciated that the pair of four grooves 240 is merely preferable and that only two or more grooves are required. As described above, the tongues 234 engage with one of the pair of grooves 240 to lock the cushion frame 212 and frame 217 against pivotal movement therebetween at a predetermined angle. It should be appreciated that the positioning of the tongues/grooves may be reversed, e.g., the tongues may be on the joining member 214 and the grooves 240 may be on the cushion frame 212. Also, the joining member 214 and cushion frame 212 may be structured to allow sliding movement of the cushion frame 212 with respect to the joining member 214.

Figure 77:
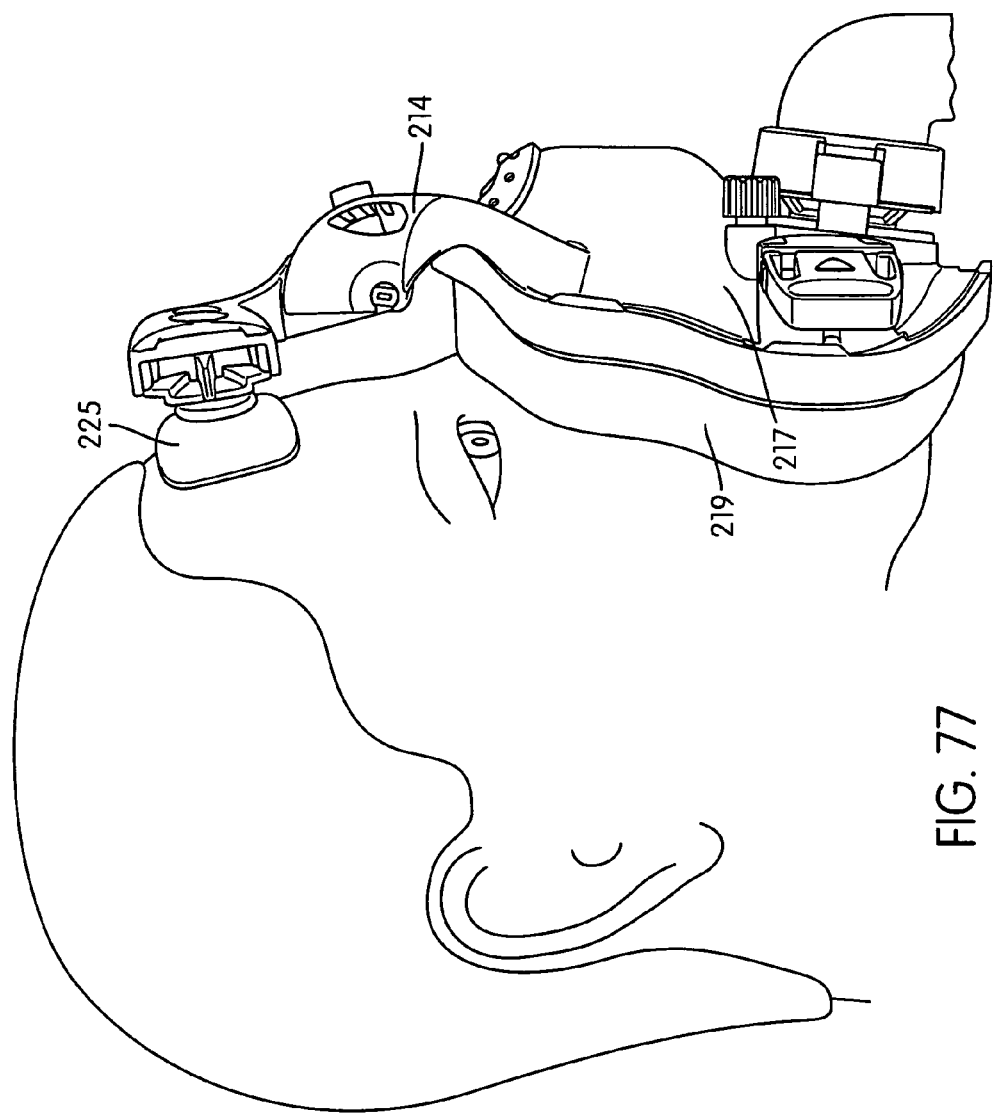
FIG. 77 is a side view of the full-face mask assembly shown in FIG. 17 engaged with a patient, the forehead support at a third of four positions.

FIGS. 21-24 illustrate different positions of the forehead support 210 with respect to the frame 217, i.e., tongues 234 engaged in first, second, third, and fourth of the four pairs of grooves 240. Also, FIGS. 75-78 show the forehead support 210 and frame 217 adjacent a patient's face with the tongues 234 engaged in first, second, third, and fourth of the four pairs of grooves 240. In use, the angle between the forehead support 210 and frame 217 can be decreased to suit patients with relatively low nasal regions and relatively high foreheads (FIGS. 75-76) and increased to suit patients with relatively high nasal regions and relatively low foreheads (FIGS. 77-78).

Figure 47:
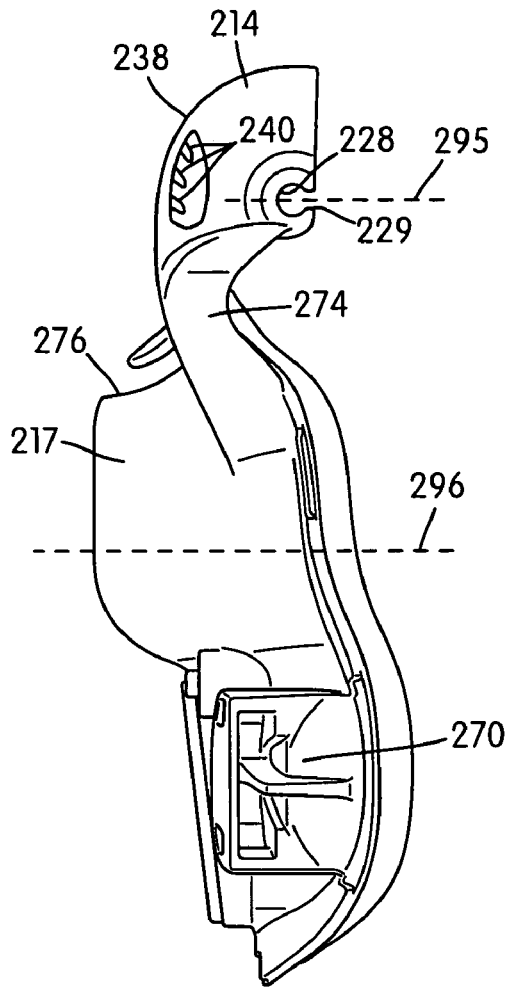
FIG. 47 is a side view of the frame shown in FIG. 43.
Figure 48:
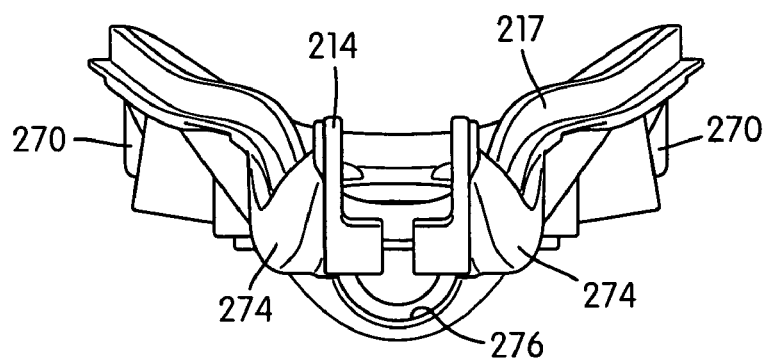
FIG. 48 is a top view of the frame shown in FIG. 43.
Figure 49:
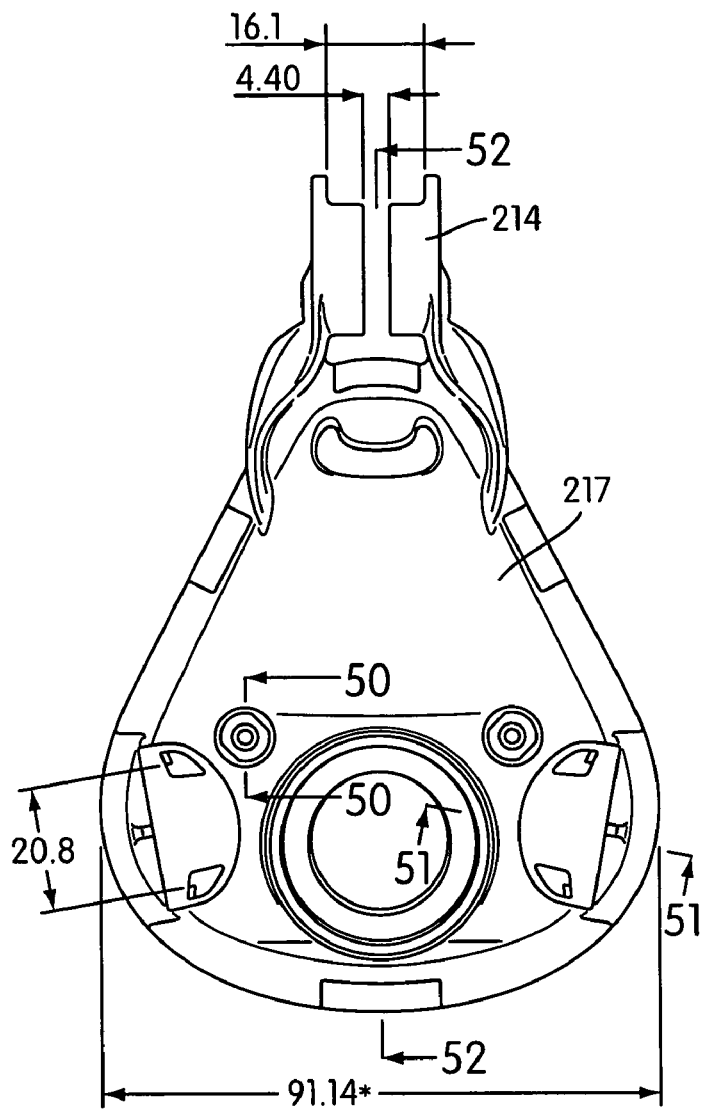
FIG. 49 is a front view illustrating an embodiment of a small size frame for a full-face mask assembly.
Figure 50:
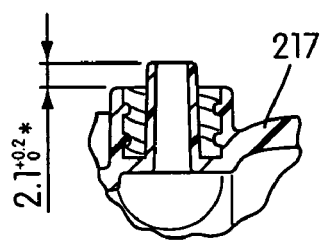
FIG. 50 is a cross-section taken along line 50-50 of FIG. 49.
Figure 51:
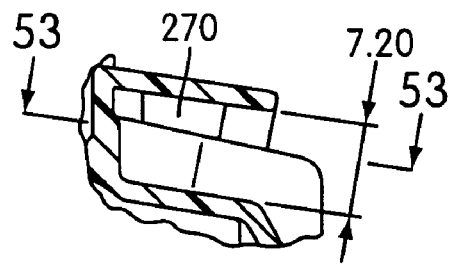
FIG. 51 is a cross-section taken along line 51-51 of FIG. 49.
Figure 52:
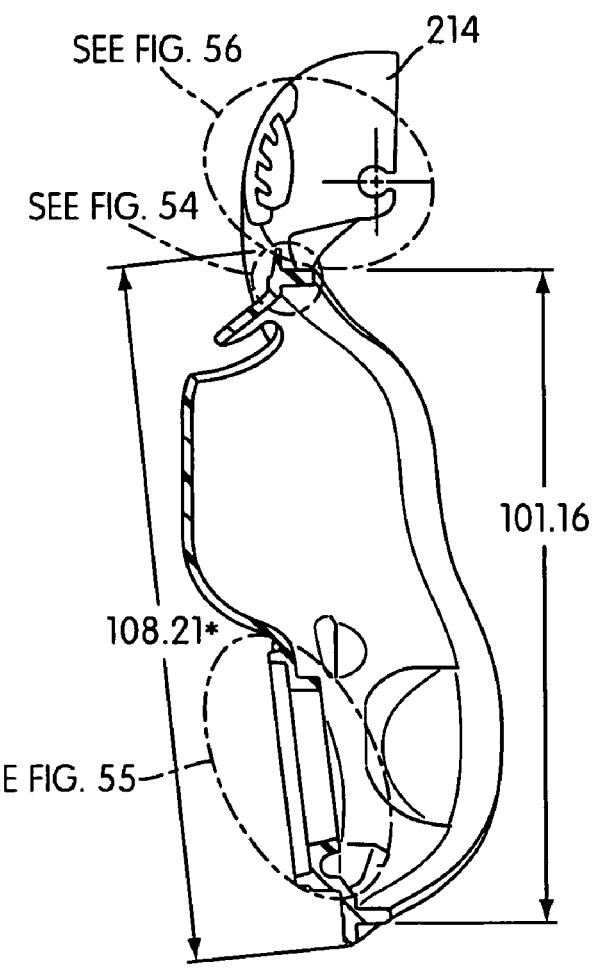
FIG. 52 is a cross-section taken along line 52-52 of FIG. 49.
Figure 53:
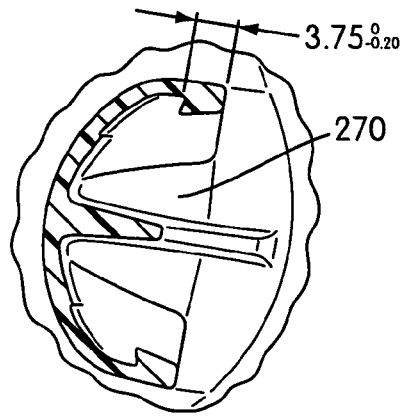
FIG. 53 is a cross-section taken along line 53-53 of FIG. 51.
Figure 54:
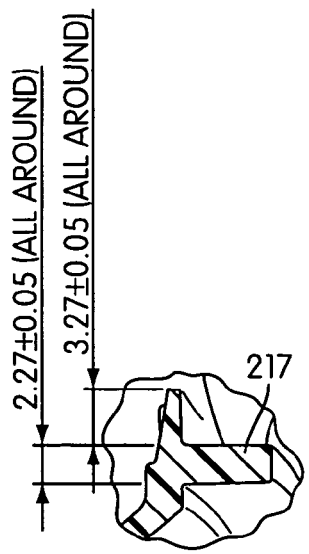
FIG. 54 is an enlarged view of FIG. 52.
Figure 55:
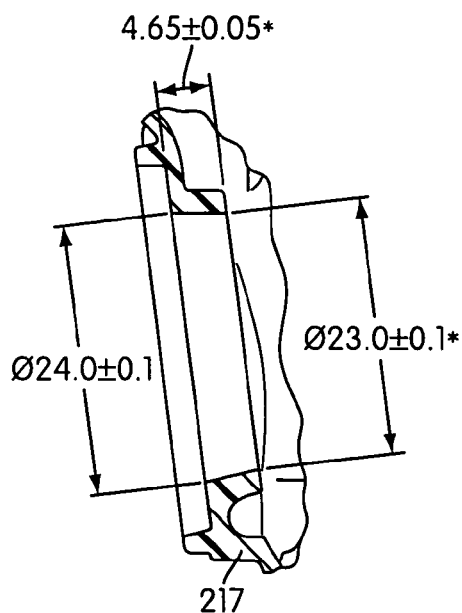
FIG. 55 is an enlarged view of FIG. 52.
Figure 56:
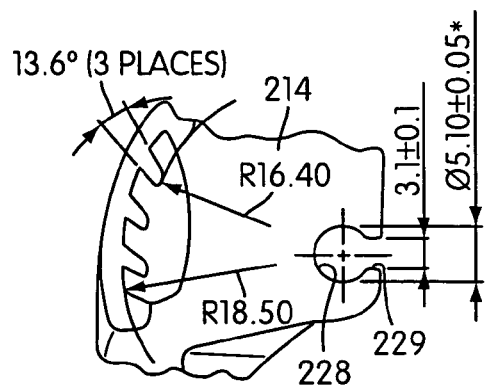
FIG. 56 is an enlarged view of FIG. 52.
Figure 57:
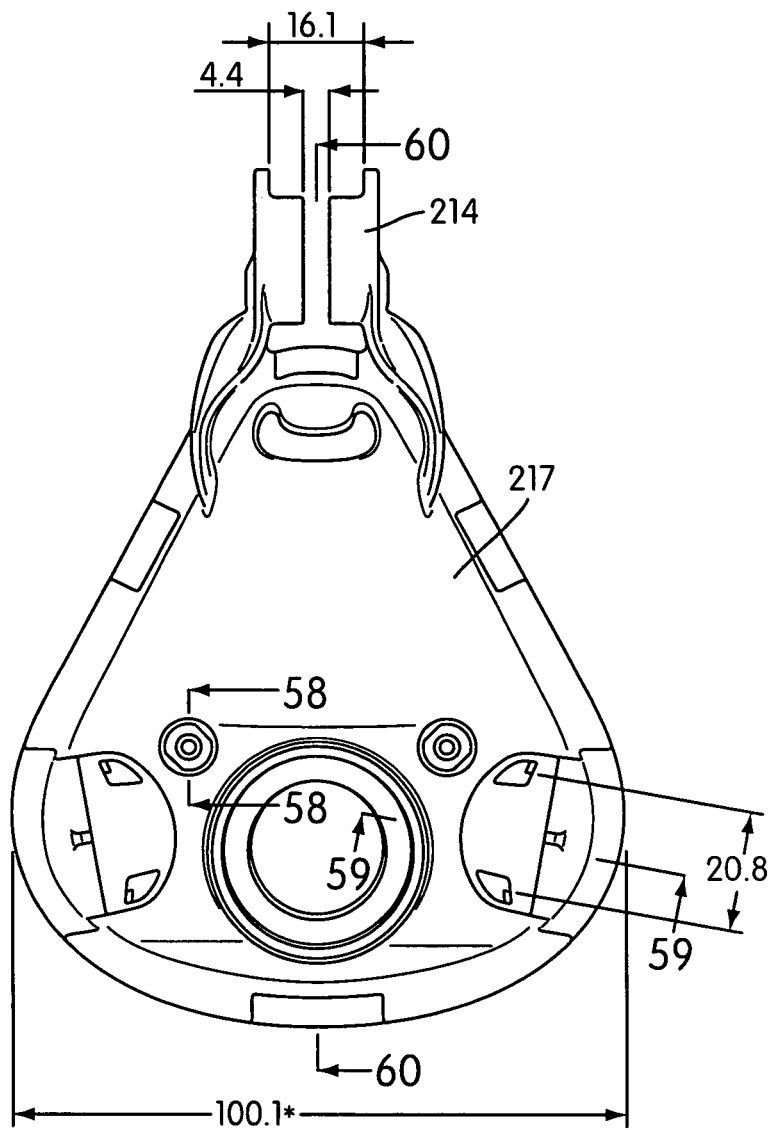
FIG. 57 is a front view illustrating an embodiment of a medium size frame for a full-face mask assembly.
Figure 58:
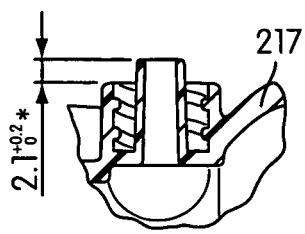
FIG. 58 is a cross-section taken along line 58-58 of FIG. 57.
Figure 59:
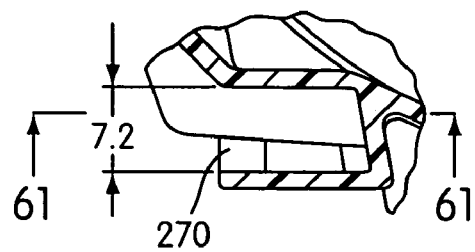
FIG. 59 is a cross-section taken along line 59-59 of FIG. 57.
Figure 60:
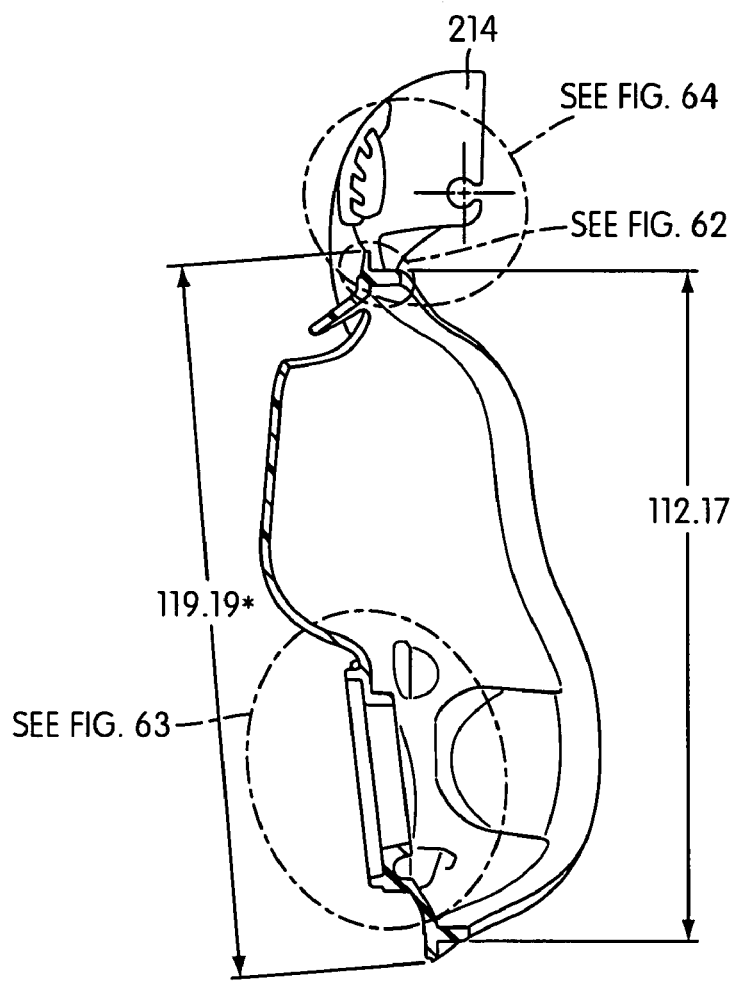
FIG. 60 is a cross-section taken along line 60-60 of FIG. 57.
Figure 61:
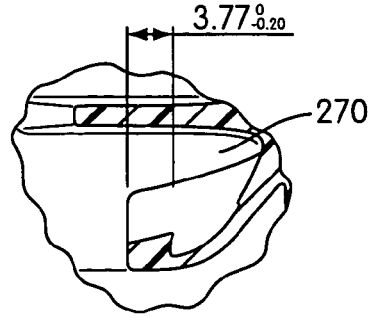
FIG. 61 is a cross-section taken along line 61-61 of FIG. 59.
Figure 62:
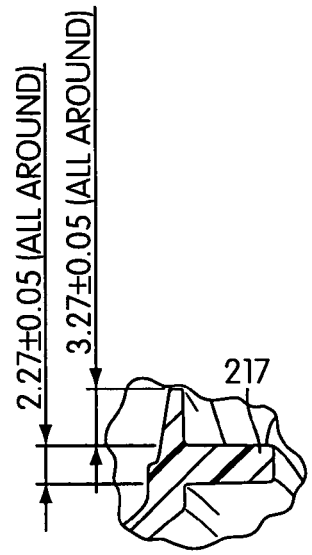
FIG. 62 is an enlarged view of FIG. 60.
Figure 63:
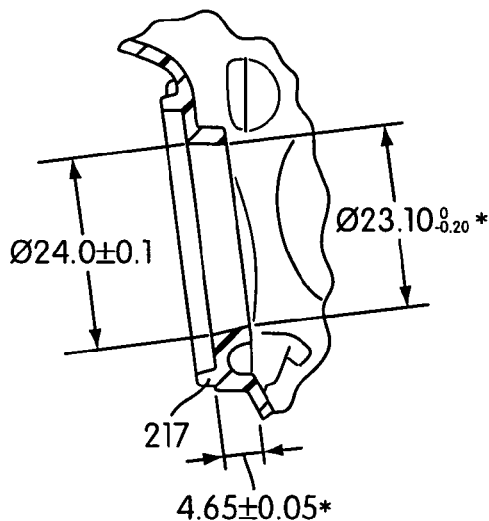
FIG. 63 is an enlarged view of FIG. 60.
Figure 64:
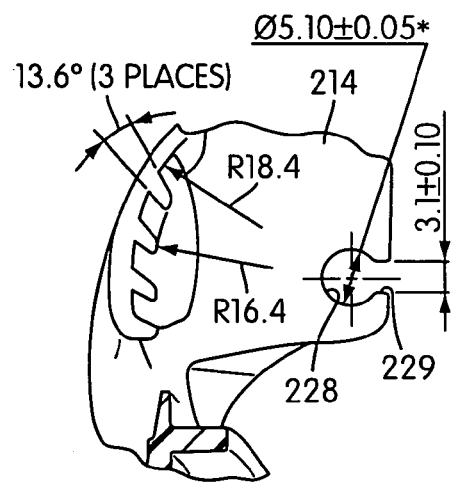
FIG. 64 is an enlarged view of FIG. 60.
Figure 65:
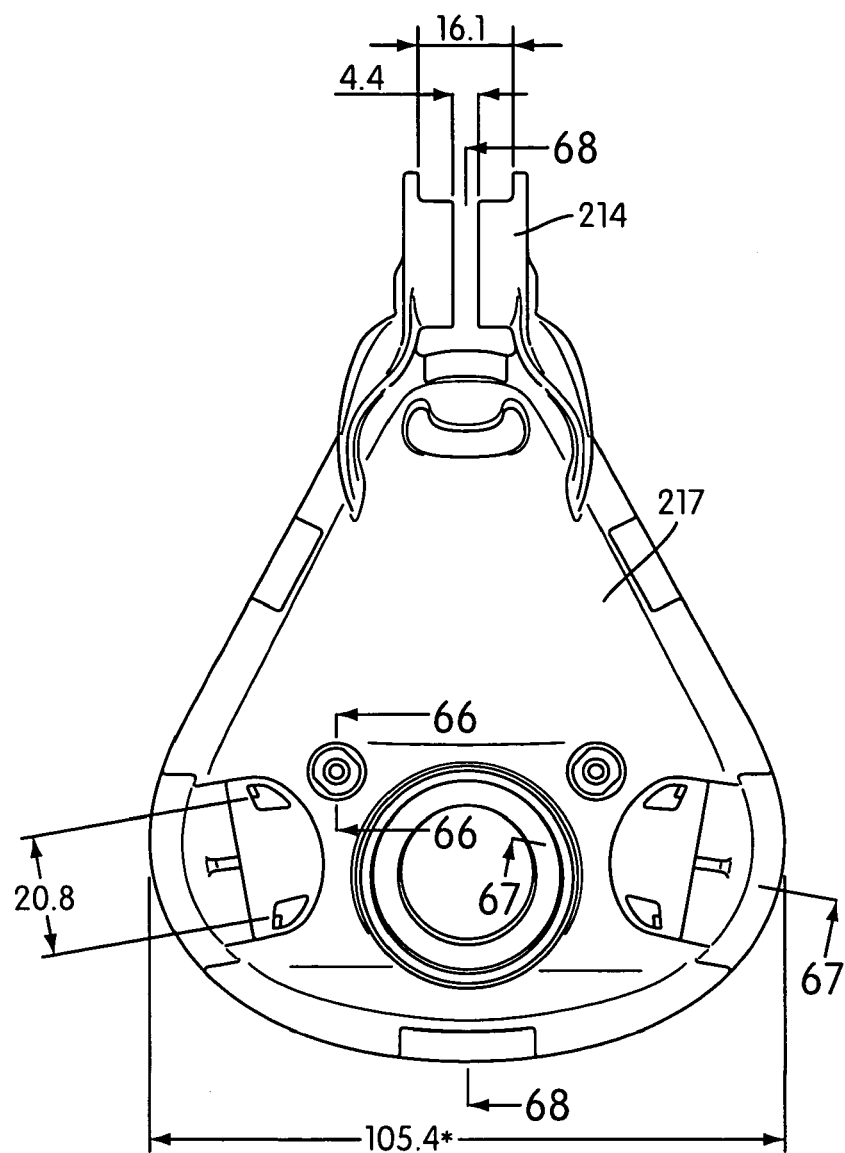
FIG. 65 is a front view illustrating an embodiment of a large size frame for a full-face mask assembly.
Figure 66:
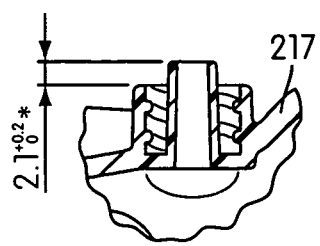
FIG. 66 is a cross-section taken along line 66-66 of FIG. 65.
Figure 67:
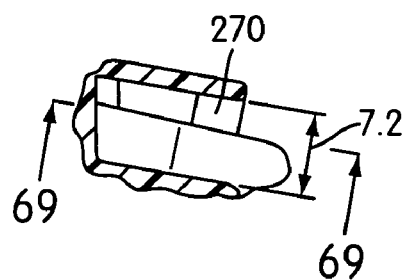
FIG. 67 is a cross-section taken along line 67-67 of FIG. 65.
Figure 68:
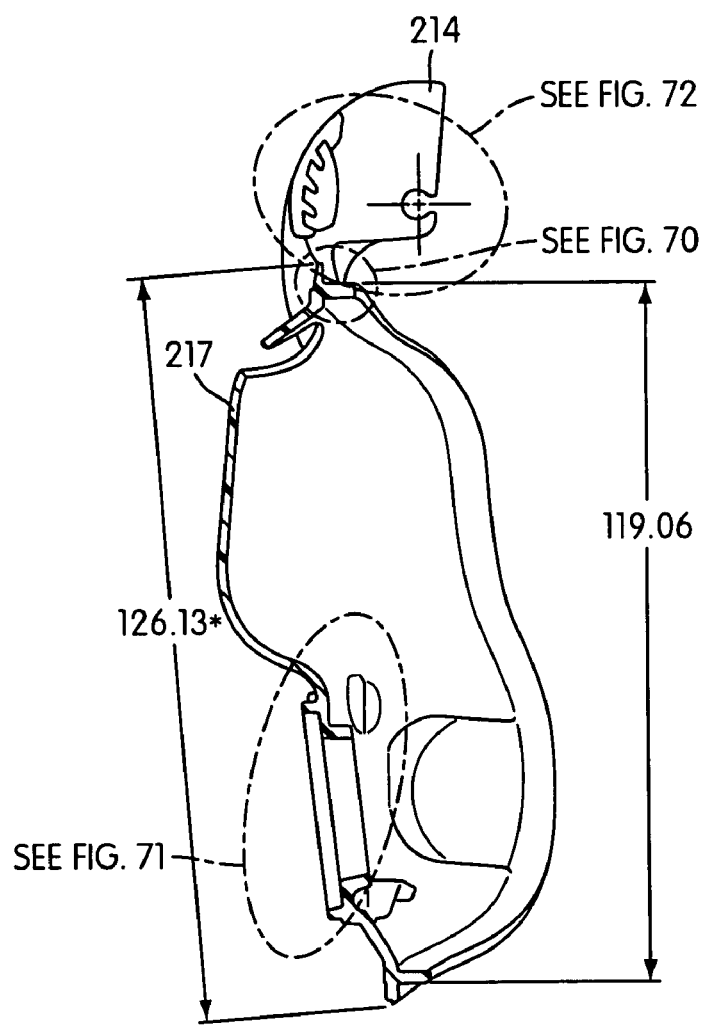
FIG. 68 is a cross-section taken along line 68-68 of FIG. 65.
Figure 69:
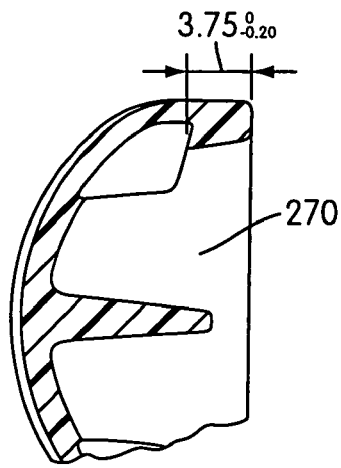
FIG. 69 is a cross-section taken along line 69-69 of FIG. 67.
Figure 70:
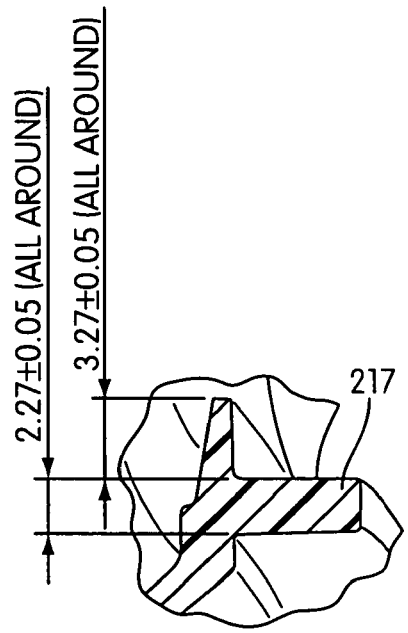
FIG. 70 is an enlarged view of FIG. 68.
Figure 71:
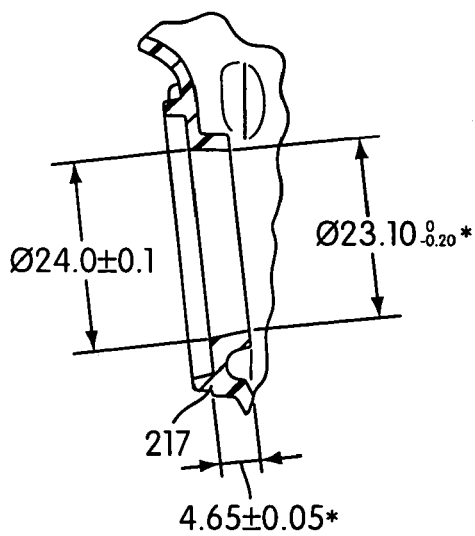
FIG. 71 is an enlarged view of FIG. 68.
Figure 72:
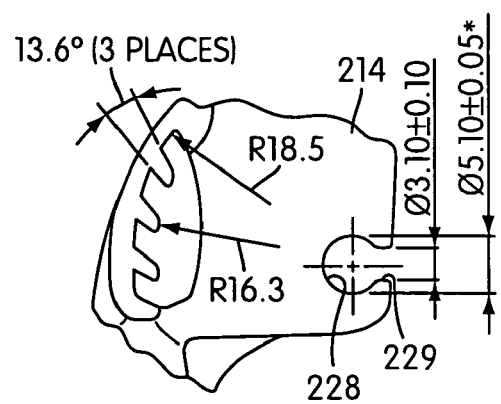
FIG. 72 is an enlarged view of FIG. 68.

As shown in FIG. 47, the openings 228 in the joining member 214 are smaller than the openings 28 in the embodiment of joining member 14 in FIGS. 15-16 so as to coincide with the smaller shafts 227 on the cushion frame 212. For example, as shown in FIGS. 56, 64, and 72, the openings 228 in joining member 214 are about 5 mm in diameter. In contrast, the openings in joining member 14 were about 6.5 mm in diameter. As a result, the joining member 214 of the frame 217 has a reduced thickness which reduces the profile of the mask. As a result, more clearance or spacing is provided between the joining member 214 and the patient's forehead (see FIGS. 75-78). This ensures that the joining member 214 does not interfere with the patient's forehead or nasal bridge.

Also, the slots 229 provided in the joining member 214 that lead to the openings 228 have a central axis 295 that is substantially parallel to a horizontal axis 296 of the frame 217 (as viewed in FIG. 47). In the embodiment of forehead support 10, the slots 29 had a central axis 95 that was angled, i.e., downwardly, with respect to a horizontal axis 96 of the frame 17 (as viewed in FIG. 15). This change in geometry facilitates assembly of the forehead support 210 to the joining member 214 and also helps increase clearance as described above.

Specifically, with the change of geometry of the shafts 227 of T-shaped cushion frame 212 and the slots 229 in the openings 228 of the joining member 214, the vertical axis 290 of the cushion frame 212 (FIG. 30) can be positioned about 90° with respect to the joining member 214 to insert the shafts 227 through respective slots 229 and into respective openings 228. As a result, the forehead support 210 can be easily assembled to and disassembled from the frame 217 with the forehead cushion 225 attached thereto. In the previous embodiments, the shafts 27 of the cushion frame 12 and slots of the openings 28 were angled such that the forehead cushions 25 may interfere with the cushion 19 on the shell 17 when the forehead support 10 was assembled to or disassembled from the joining member 14.

Figure 44:
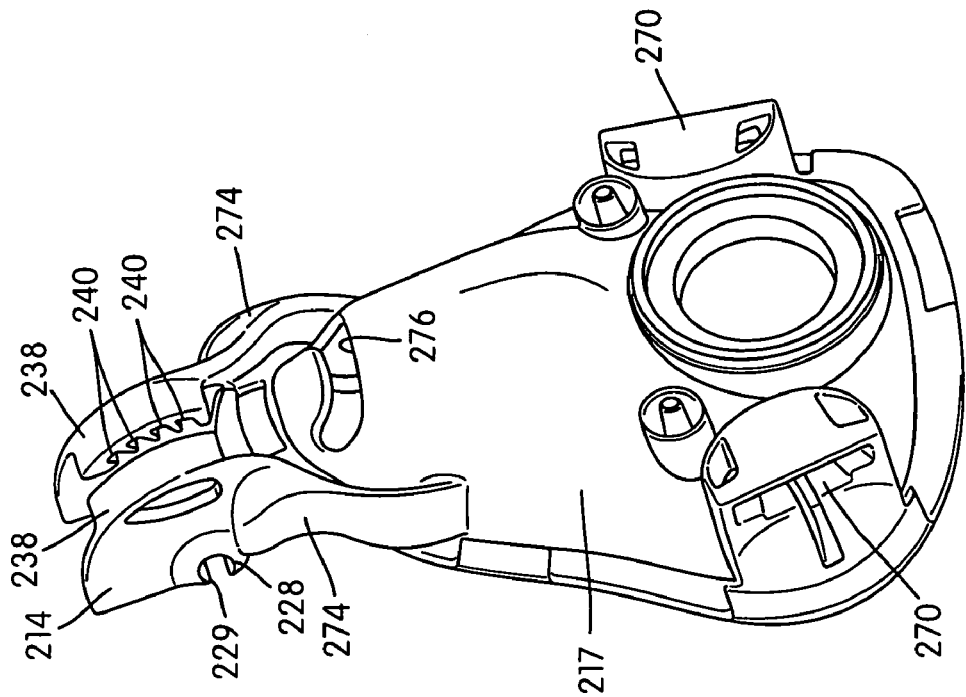
FIG. 44 is a front perspective view, similar to FIG. 43 but at a different angle, of the frame shown in FIG. 43.
Figure 43:
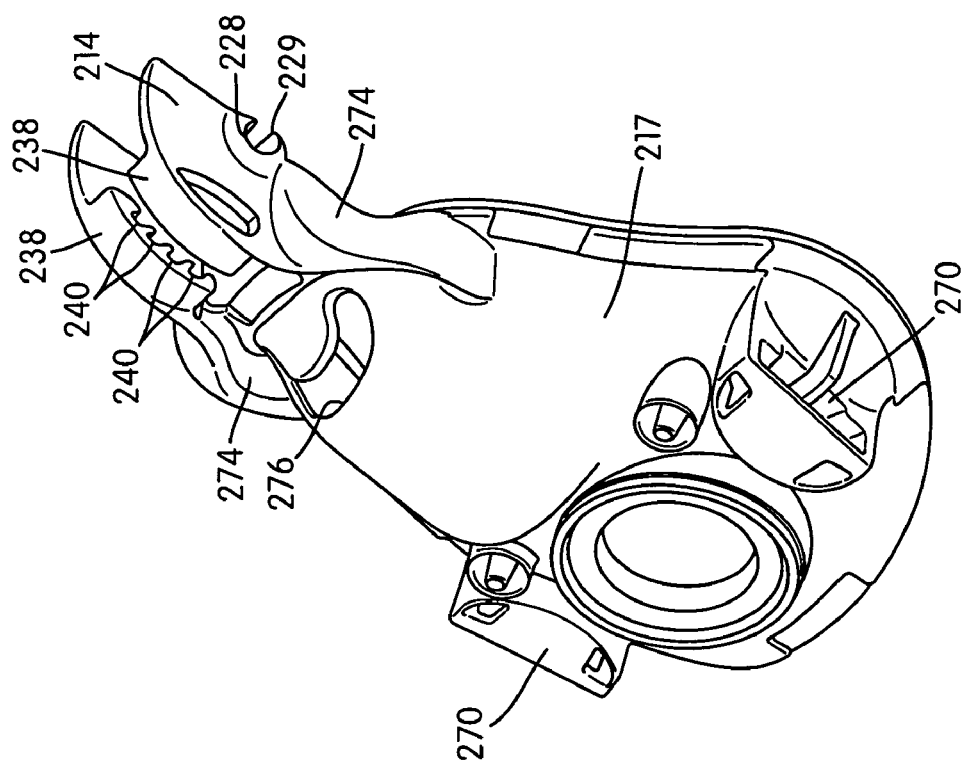
FIG. 43 is a front perspective view of the frame shown in FIG. 20.
Figure 45:
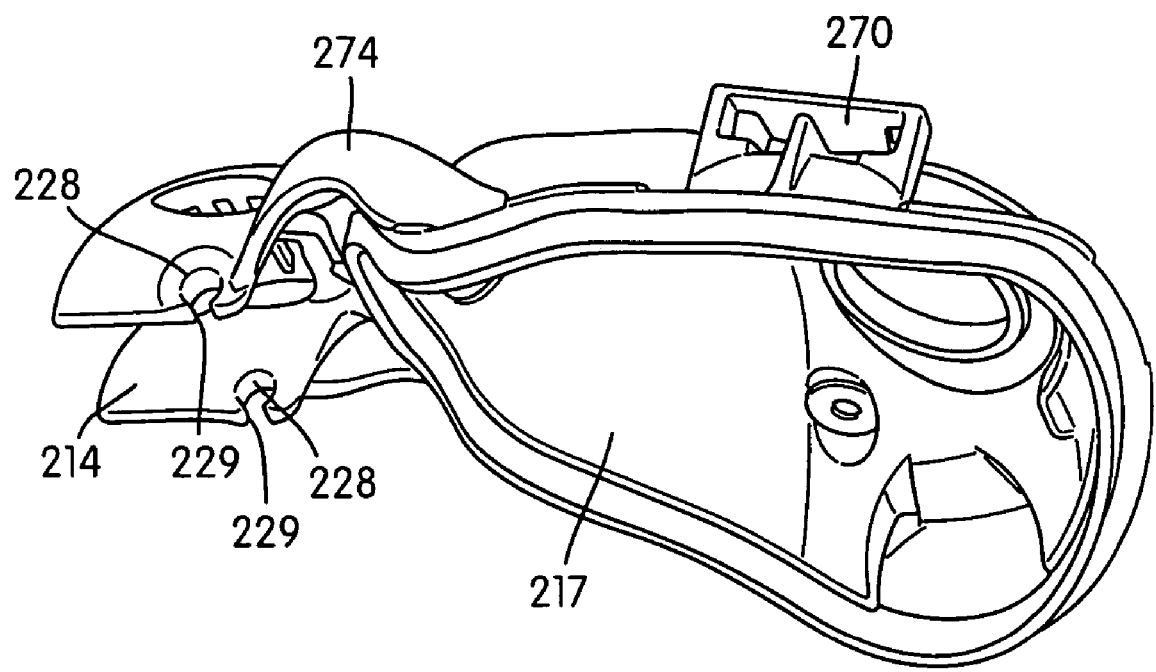
FIG. 45 is a rear perspective view of the frame shown in FIG. 43.
Figure 46:
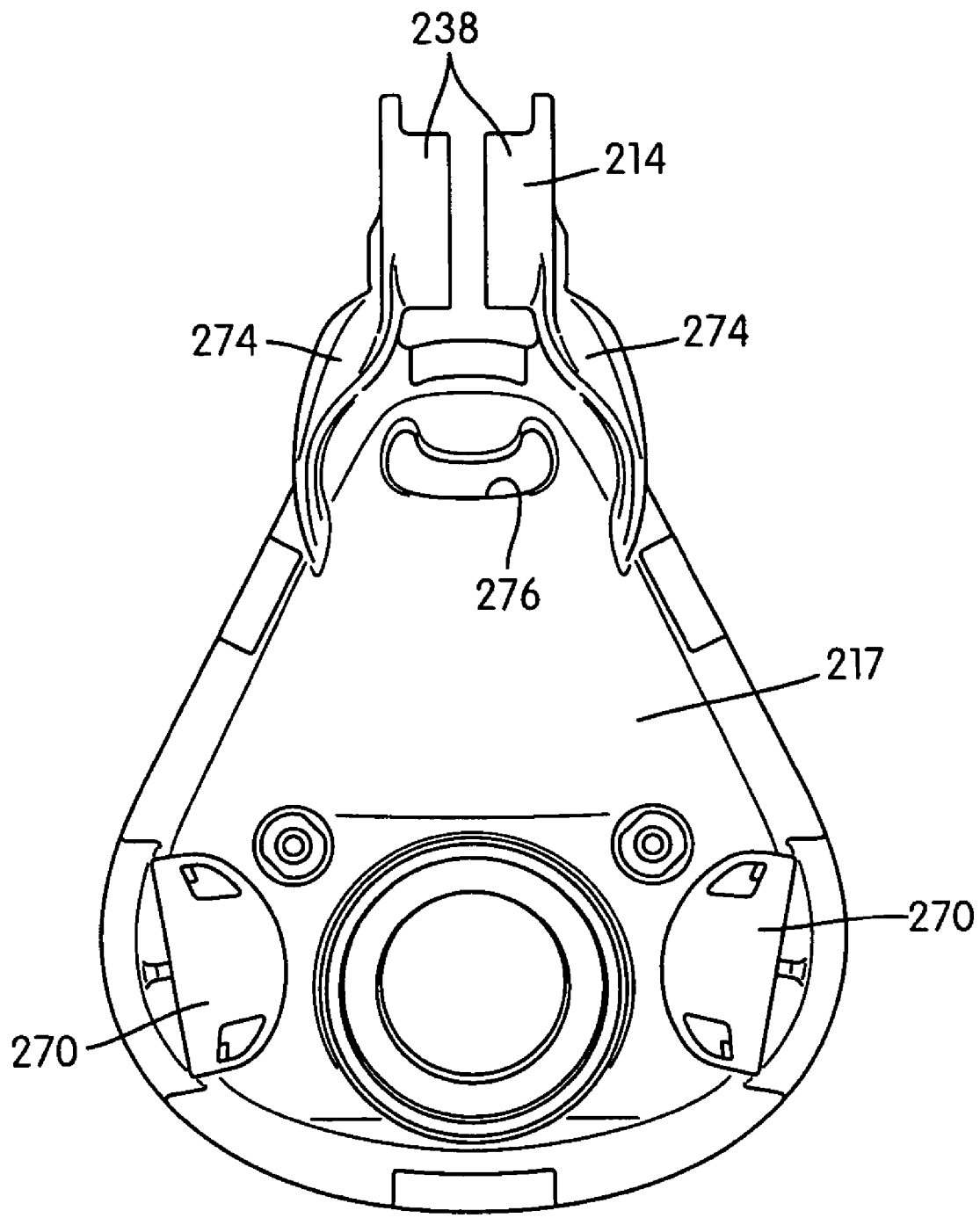
FIG. 46 is a front view of the frame shown in FIG. 43.

Further, as best shown in FIGS. 43, 44, and 46, the joining member 214 includes additional support members 274. The support members 274 add lateral support to the joining member 214.

The support members 274 also function to space the joining member 214 away from a vent 276 provided in an upper portion of the frame 217 so that the joining member 214 does not occlude the vent 276. Noise from air exiting the vent 276 is also reduced by spacing the joining member 214 away from the vent 276. In use, a vent cover 278 (see FIGS. 18 and 19) is attached to the vent 276 to quiet exiting air away from the joining member 214 (as disclosed in Australian Patent No. 712236 and U.S. application Ser. No. 09/021,541 the entireties of which are herein incorporated by reference).

The frame 217 for the full-face mask assembly 200 may come in different sizes, e.g., small, medium, and large, to accommodate a wide range of patients. The same forehead support 210 may be used with the different sizes of frames 217. For example, FIGS. 49-56 show further structural details and various dimensions in one embodiment of a small size frame for a full-face mask assembly. FIGS. 57-64 show further structural details and various dimensions in one embodiment of a medium size frame for a full-face mask assembly. FIGS. 65-72 show further structural details and various dimensions in one embodiment of a large size frame for a full-face mask assembly. As illustrated, the small size frame has a width of about 91 mm and height of about 108 mm (minus the joining member), the medium size frame has a width of about 100 mm and height of about 119 mm (minus the joining member), and the large size frame has a width of about 105 mm and height of about 126 mm (minus the joining member). In the embodiments of frames 217, the dimensions illustrated in FIGS. 49-72 may vary up to ±10%, or more.

While the illustrated embodiment shows pivotal movement about a shaft in a cushion frame, a number of different mechanisms may be used to facilitate angular movement of the forehead support. For example, the shaft may be located on the joining member, rather than the cushion frame. Alternatively, angular movement of the forehead support may be provided by sliding of the frame with respect to the shaft. The frame may pivot about a point not physically located within the mask assembly. Furthermore, locking of the angular position of the frame with respect to the joining member may be accomplished by mechanisms other than a push-button. In one form, the forehead support may be selectively lockable in one position and free to pivot to other angular positions. Also, the forehead cushion may have corresponding openings, rather than the cushion frame.

It can thus be appreciated that the aspects of the present invention have been fully and effectively accomplished. The foregoing specific embodiments have been provided to illustrate the structural and functional principles of the present invention, and are not intended to be limiting. To the contrary, the present invention is intended to encompass all modifications, alterations and substitutions within the spirit and scope of the detailed description.

What is claimed is:

1. A respiratory mask assembly for delivering breathable gas to a patient, comprising:
    a frame; and
    a forehead support secured to the frame, the forehead support including:
        a joining member secured to an upper portion of the frame; and
        a cushion frame movably mounted to the joining member;
        one of the joining member and the cushion frame including a pair of shafts and the other of the joining member and the cushion frame including a pair of openings, the pair of shafts being respectively received in the pair of openings to couple the cushion frame to the joining member and enable the cushion frame to move relative to the joining member;
    wherein each of the shafts has a non-circular cross section including longitudinal edges that define a major longitudinal axis therebetween, the major longitudinal axis being angled forwardly of a vertical axis of one of the joining member and the cushion frame so as to angle toward a front portion of one the joining member and the cushion frame.

2. A respiratory mask assembly according to claim 1, wherein the mask assembly is a full-face mask.

3. A respiratory mask assembly according to claim 1, wherein the cushion frame is lockable at two or more predetermined angular positions relative to the joining member using a spring-based push-button associated with the cushion frame.

4. A respiratory mask assembly according to claim 1, wherein each of the frame and cushion frame include a locking clip receiver assembly structured to interlock with a locking clip associated with a headgear assembly.

5. A respiratory mask assembly according to claim 1, wherein each of the shafts has a diameter of about 5 mm and a width of about 3 mm.

6. A respiratory mask assembly according to claim 1, wherein each of the shafts is angled about 15° forwardly of the vertical axis.

7. A respiratory mask assembly according to claim 1, wherein each of the openings has a diameter of about 5 mm.

8. A respiratory mask assembly according to claim 1, wherein one of the joining member and the cushion frame includes a pair of slots that lead to the pair of openings, the pair of slots being substantially parallel to a horizontal axis of the one of the joining member and the cushion frame.

9. A respiratory mask assembly according to claim 1, wherein the joining member includes a pair of support members that space the joining member away from a vent provided in an upper portion of the frame.

10. A respiratory mask assembly according to claim 1, wherein the cushion frame includes one or more openings structured to receive one or more forehead cushions, the one or more openings being angled downwardly, as viewed from the side, so as to properly orient the one or more forehead cushions with respect to the patient's forehead in use.

11. A respiratory mask assembly according to claim 1, wherein the cushion frame includes the pair of shafts on a lower portion thereof and the joining member includes the pair of openings.

12. A method for assembling a respiratory mask assembly including a frame and a forehead support, comprising:
    providing a pair of slots that lead to a pair of openings in one of the frame and the forehead support;
    providing a pair of shafts on the other of the frame and the forehead support;
    orienting a vertical axis of one of the frame and the forehead support about 90° with respect to the other of the frame and the forehead support;

inserting the pair of shafts through the pair of slots and into the pair of openings; and pivoting the forehead support about a pivot axis defined by the pair of shafts to assemble the forehead support to the frame.

13. A method according to claim 12, wherein providing a pair of shafts includes providing a pair of shafts each having a non-circular cross section including longitudinal edges that define a major longitudinal axis therebetween.

14. A method according to claim 12, wherein the pair of shafts each include a first dimension equal to or less than a width of the respective slot and a second dimension greater than the first dimension, and the method further includes:

inserting each of the pair of shafts such that the first dimension is aligned with and guided through the respective slot and into the respective opening, and rotating the forehead support such that the second dimension of each of the pair of shafts extends across the respective slot to prevent inadvertent withdrawal of the pair of shafts from the pair of openings.

15. A method according to claim 12, wherein providing a pair of slots includes providing a pair of slots that lead to a pair of substantially circular openings in one of the frame and the forehead support.

16. A respiratory mask assembly according to claim 1, wherein the front portion is adapted to face outwardly from the patient.

17. A respiratory mask assembly according to claim 1, wherein the openings are circular.

18. A respiratory mask assembly according to claim 1, wherein the shafts are adapted to rotate in respective openings to provide rotational movement of the cushion frame relative to the joining member about a pivot axis defined by the pair of shafts.

* * * * *